(12) United States Patent
Kirkpatrick

(10) Patent No.: US 6,552,060 B1
(45) Date of Patent: Apr. 22, 2003

(54) ASYMMETRIC DISULFIDES AND METHODS OF USING SAME

(75) Inventor: D. Lynn Kirkpatrick, Emerald Park (CA)

(73) Assignee: Prolx Pharmaceuticals, Inc., Tuscon, AZ (US)

( * ) Notice: Subject to any disclaimer, the term of this patent is extended or adjusted under 35 U.S.C. 154(b) by 0 days.

(21) Appl. No.: 09/132,421

(22) Filed: Aug. 11, 1998

Related U.S. Application Data
(60) Provisional application No. 60/055,201, filed on Aug. 11, 1997.

(51) Int. Cl.$^7$ .................... A61K 31/415; C07D 233/30; C07D 233/66
(52) U.S. Cl. ...................... 514/398; 514/396; 548/325.1
(58) Field of Search ....................... 514/396; 548/325.11

(56) References Cited

U.S. PATENT DOCUMENTS

| | | | |
|---|---|---|---|
| 4,149,003 A | | 4/1979 | Carlsson et al. ............. 546/261 |
| 4,188,488 A | | 2/1980 | Dubs et al. ................. 548/337 |
| 4,324,793 A | * | 4/1982 | Hagen et al. ................ 424/270 |
| 5,338,542 A | | 8/1994 | Thorpe et al. ............ 424/180.1 |
| 5,416,064 A | | 5/1995 | Chari et al. .............. 514/229.5 |
| 5,475,092 A | | 12/1995 | Chari et al. .............. 530/391.7 |
| 5,633,274 A | | 5/1997 | Halperin et al. ............ 514/405 |
| 5,645,988 A | | 7/1997 | Vande Woude et al. ......... 435/6 |
| 5,756,068 A | | 5/1998 | Jimbow ..................... 424/1.81 |

FOREIGN PATENT DOCUMENTS

| | | |
|---|---|---|
| WO | 98/00160 | 1/1998 |
| WO | 98/24472 | 6/1998 |
| WO | 98/29449 | 7/1998 |

OTHER PUBLICATIONS

Kunkel et al, Anti–Cancer Drug Design #12, 659–670, 1997.*
Kirkpatrick et al 116CA:255539, 1992.*
Beer et al 92CA:110932, 1979.*
Laurent, T.C. et al. Enzymatic Synthesis of deoxyribonucleotides VI. Isolation and Characterization of Thioredoxin, the Hydrogen Donor from *Escherichia coli* B. J. Biol. Chem. 239 (1964):3436–44.
Krohne–Enrich G. et al. Glutathione Reductase from Human Erythrocytes. Isolation of the Enzyme and sequence analysis of the redox–active paptide. Eur. J. Biochem. 80 (1971): 65–71.
Grippo, J.F. et al. Evidence that the Endogenous Heat–Stable Glucocorticoid Receptor–Activating Factor is Thioredoxin. J. Biol. Chem. 258 (1983): 13658–64.
Holmgren, A. et al. Thioredoxin. Ann. Rev. Biochem. 54 (1985): 237–71.
Kirkpatrick, D.L. Modification of Antitumor Disulfide cytotoxicity by Glutathione Depletion. Cancer Res. 47 (1987): 4391–95.

Silverman, R.B. et al. Reduced Thioredoxin: A Possible Physiological Cofactor for Vitamin K Epoxide Reductase. Further Support for an Active Site Disulfide. Biochem. Biophys. Res. Commun. 155 (1988): 1248–54.
Boyd, M.R. Status of Implementation of the NCI Human Tumor Cell in Line in vitro Primary Drug Screen. Proc Am. Assoc. Cancer Res. 30 (1989): 652–54.
Coshan–Gauthier, R. et al. Modulation of Disulfide Antitumor Activity in Balb/c mice through Glutathione Depletion. Exp. Cell Biol. 57 (1989): 273–80.
Cromlish, J.A. et al. Human Transcription Factor IIIC (TFIIIC). Purification, Polypeptide Structure, and the Involvement of Thiol Groups in Specific DNA Binding. J. Biol. Chem. 264 (1989): 18100–109.
Kirkpatrick, D.L. Kinetic Studies of the Interaction of Glutathione with Four Antitumor Disulfides: Possible Mechanism for cellular GSH depletion. Chem. Biol. Interact. 69 (1989): 225–34.
Kirkpatrick, D.L. et al. Inhibitory Effect of Cytotoxic Disulfides on membrane Na+/K+ ATPase. Biochem. Pharmacol. 39 (1990): 1484–87.
Lundstrom, J. et al. Protein Disulfide–isomerase is a Substrate for Thioredoxin reductse and has Thioredoxin–like Activity. J. Biol. Chem. 265 (1990) :9114–20.
Wakasugi, N. et al. Adult T–Cell Leukemia derived factor/thioredoxin produced by both human T–lymphotropic Virus Type 1 and Epstein–Barr virus–transformed lymphocytes, acts as an autocrine growth factor and synergized with interleuki–1 and interluken–2. Proc. Natl. Acad. Sci. USA 87 (1990): 8282–86.
Fujii, S. et al. Coexpression of Adult T–Cell Leukemia–derived factor, a Human Thioredoxin Homologue, and Human Papillomavirus DNA in Neoplastic Cervical Squamous Epithelium. Cancer 68 (1991):1583–91.
Yodoi, J. et al. ADF a Growth–Promoting Factor Derived from Adult T–Cell Leukemia and Homologous to Thioredoxin: Involvement in Lymphocyte Immortalization by HTLV–1 and EBV. Adv. Cancer Res. 57 (1991): 381–411.
Ericson, M.L. et al. Secretion of Thioredoxin After in vitro Activation of Human B Cells. Lymphokine Cytokine Res. 11 (1992): 201–07.
Fountoulakis, M. et al. Unfolding Intermediates of the Extracellular Domain of the Interferon Gamma Receptor. J. Biol. Chem. 267 (1992): 7095–7100.

(List continued on next page.)

*Primary Examiner*—Russell Travers
(74) *Attorney, Agent, or Firm*—Raymond A. Miller; Pepper Hamilton LLP

(57) ABSTRACT

The present invention is directed to a composition or formulation which includes an asymmetric disulfide which alone or in combination inhibits or interferes with cellular redox function, as well as a method of using same to restore normal cellular function. More specifically, the composition of the present invention interacts with, interferes with or inhibits abnormal cellular proliferation and restores or prevents inhibition of cellular apoptosis.

19 Claims, 11 Drawing Sheets

OTHER PUBLICATIONS

Kirkpatrick, D.L. et al. Effect of a Hypoxic Tumor Cell Cytotoxic Disulfide on the Membrane and DNA of Tumor Cells in Culture. Anticancer Drugs 3 (1992): 651–58.

Kirkpatrick, D.L. et al. Synthesis and Evaluation of Imidazolyl Disulfides for Selective Cytotoxicity to Hypoxic EMT6 Tumor Cells in vitro. Euro. J. Med. Chem. 27 (1992): 33–37.

Matthews, J.R. et al. Thioredoxin Regulates the DNA Binding Activity of NF–KappaB by Reduction of a Disulphide Bond Involving Cysteine 62. Nucleic Acids Res. 20 (1992): 3821–30.

Nakamura, H. et al. Expression and Growth–Promoting Effect of Adult T–Cell Leukemia–derived Factor. A Human Thioredoxin Homologue in Hepatocellular Carcinoma. Cancer 69 (1992): 2091–97.

Paull, K.D. e t al. Identification of Novel Antimitotic Agents acting at the Tubulin Level by Computer–Assisted Evaluation of Differential Cytotoxicity Data. Cancer Res. 52 (1992): 3892–3900.

Rubartelli, A. et al. Secretion of Thioredoxin by Normal and Neoplastic Cells Through a Leaderless Secretory Pathway. J. Biol. Chem. 267/34 (Dec. 5, 1992): 24161–64.

Hayashi, T. Oxidoreductive Regulation of Nuclear Factor KappaB: Involvement of a Cellular Reducing Catalyst Thioredoxin. J. Biol. Chem. 268 (1993): 11380–388.

Oblong, J.E. et al. Purification of Human Thioredoxin Reductase: Properties and Characterization by Absorption and Circular Dichroism Spectroscopy. Biochemistry 32 (1993): 7271–77.

Wang, Y. et al. Wild–type p53–triggered apoptosis is inhibited by bcl–2 in a v–myc–induced T–Cell Lymphoma Line. Oncogene 8 (1993): 3427–31.

Galter, D. et al. Distinct Effects of Glutathione Disulfide on the Nuclear Transcription Factors KappaB and the Activator Protein–1. Eur. J. Biochem. 221 (1994): 639–48.

Gasdaska, P.Y. et al. The Predicted Amino Acid Sequence of Human Thioredoxin is identical to that of the Autocrine Growth Factor Human Adult T–Cell Derived Factor (ADF): Thioredoxin mRNA is Elevated in Some Human Tumors. Biochem. Biophys. Acta 1218 (1994): 292–96.

Kirkpatrick, D.L. et al. Disulfide Cytotoxicity Under Hypoxia. Oncol. Res. 6/10–11 (1994): 545–52.

Oblong, J.E. et al. Site–directed Mutagenesis of Active Site Cysteines in Human Thioredoxin Produces Competitive Inhibitors of Human Thioredoxin Reductase and Elimination of Mitogenic Properties of Thioredoxin. J. Biol. Chem. 269 (1994): 11714–720.

Oblong, J.E. et al. Reversible Inhibition of Human Thioredoxin Reductase Activity by Cytotoxic Alkyl 2–imidazoly Disulfide Analogues. Cancer Chem. Pharmacol. 34 (1994): 434–38.

Powis, G. et al. The Thioredoxin/Thioredoxin Reductase Redox System and Control of Cell Growth. Oncol. Res. 6/10–11 (1994): 539–44.

Verentchikov A.N. et al. Reflecting time–of–flight mass spectrometer with an electrospray ion source and orthogonol extraction. Anal. Chem. 66 (1994): 126–133.

Gasdaska, J.R. et al. Cell Growth Stimulation by the Redox Protein Thioredoxin Occurs by a Novel Helper Mechanism. Cell Growth Differ. 6 (1995): 1642–50.

Kirkpatrick, D.L. et al. Stimulation of Apoptsis by a Redox Active Disulfide. Proc. Am. Assoc. Cancer Res. 36 (1995): 2469.

Kuperus, M. et al. Interaction of Redox Active Disulfides with the Autocrine Growth Factor, Human Thioredoxin. Proc. Am. Assoc. Cancer Res. 36 (1995): 2541.

Orr, A. et al. "Waterbug" Dialysis. Biotechniques 19 (1995): 204–206.

Rubertelli, A. et al. High Rates of Thioredoxin Secretion Correlates with Growth Arrest in Hepatoma Cells. Cancer Res. 55 (1995): 675–80.

Berggren, M. et al. Thioredoxin and Thioredoxin Reductase Gene Expression in Human Tumors and Cell Lines, and the Effects of Serum Stimulation and Hypoxia. Anticancer Res. 16 (1996): 3459–66.

Borman, S. Combinatorial Chemists Focus on Small Molecules, Molecular Recognition and Automation. Chem. Eng. News 74 (1996): 29–54.

Gallegos, A. et al. Transfection with Human Thioredoxin Increases Cell Proliferation and a Dominant–Negative Mutant Thioredoxin Reverses the Transformed Phenotype of Human Breast Cancer Cells. Cancer Res. 56/24 (Dec. 15, 1996): 5765–70.

Gasdaska, J.R. et al. Oxidative Inactivation of Thioredoxin as a Cellular Growth Factor and Protection by CYS(73)1 Ser Mutation. Biochem. Pharmacol. 52 (1996): 1741–47.

Gladyshev, V.N. et al. Selenocystein, Identified as the Penultimate C–Terminal Residue in Human T–Cell Thioredoxin Reductase, Corresponds to TGA in the Human Placental Gene. Proc. Natl. Acad. Sci USA 93 (1996): 6146–47.

Powis, G. et al. Thioredoxin Redox Signaling: A Novel Target for Anti–cancer Drug Development. Anti–Cancer Drugs 7/3 (1996): 121–26.

Weichsel, A. et al. Crystal Structures of Reduced, Oxidized and Mutated Human Thioredoxins: Evidence for a Regulatory Homodimer. Structure 4 (1996): 735–751.

Kirkpatrick, D.L. et al. Antitumor Activity of Inhibitors of a Novel Signaling Pathway: Thioredoxin/Thioredoxin Reductase. Proc. Am. Assoc. Cancer Res. 38 (1997): 4115.

Kirkpatrick, D.L. et al. Redox Control as a Target for Anticancer Drug Development. Current Pharmaceutical Design 3 (1997): 305–22.

Kirkpatrick, D.L. et al. Redox Active Disulfides: The Thioredoxin System as a Drug Target. Oncology Research 9 (1997): 351–56.

Kunkel, M.W. et al. Cell Line–Directed Screening Assay for Inhibitors of Thioredoxin Reductace Signaling as Potential Anti–Cancer Drugs. Anti–Cancer Drug Design 12 (1997) 659–70.

Kirkpatrick, D.L. et al. Mechanisms of Inhibition of the Thioredoxin Growth Factor System by Antitumor 2–Imidazolyl Disulfides. Biochemical Pharmacology 55 (1998): 987–94.

* cited by examiner

R =

1  2  3  4  5  6  7

8  9  10  11  12

13  14  15  16  17  18

19  20  21  22  23  24

25  26  27  28

AA

BB

CC

DD

EE

FF

GG

HH

II

JJ

KK

ASYMMETRIC DISULFIDES AND METHODS OF USING SAME

RELATED APPLICATION

This application claims continuing status from Provisional Patent Application Ser. No. 60/055,201, filed Aug. 11, 1997.

BACKGROUND OF THE INVENTION

1. Field of the Invention

The present invention relates generally to asymmetric disulfides, and more specifically to therapeutic compositions comprised of asymmetric disulfides, said asymmetric disulfides providing a desired therapeutic activity. Preferably, the asymmetric disulfides of the present invention interact, inhibit or interfere with cellular redox systems.

2. Background of the Related Art

Cellular redox systems are important to normal cellular activity. Cells maintain an intracellular environment that is reducing in the face of a highly oxidizing extra-cellular environment. Regulated alterations in the intracellular redox state (redox signaling) can modulate cellular activity, including activities such as DNA synthesis, enzyme activation, selective gene expression, cell cycle regulation, cell growth, and programmed cell death.

One of the more important consequences of intracellular redox signaling is a change in the oxidative state of select cysteine residues on certain proteins. The post-translational modification of cysteine is, however, difficult to follow because it lacks a convenient marker and the oxidative state of cysteine is readily reversed when the cell contents are exposed to extra-cellular oxidizing conditions.

Abnormal cellular proliferation is one type of abnormal cell function. That is a cardinal feature of human malignancy. In recent years there has been great insight into the bio-molecules that regulate cell proliferation and the pathways in which they operate. These bio-molecules have been identified as pharmacological, therapeutic, and/or diagnostic targets for agents which inhibit cellular proliferation. Abnormal cellular proliferation is most often associated with cancer and other hyperproliferative diseases.

Another type of abnormal cell function is resistance to apoptosis. Apoptosis is a form of programmed cell death characterized by membrane blebbing, chromatin margination and breakdown of chromosomal DNA into nucleosome-sized fragments. Loss of apoptosis can lead to diseases such as cancer, autoimmune disease, inflammation, and hyperproliferation disease. Increased apoptosis can lead to neurodegenerative disease and destruction of tissue, as well as cardiovascular damage. Normally, when a cell sustains substantial genetic damage that cannot be repaired through normal DNA repair processes, sensory mechanisms in the cell recognize this and initiate a sequence of events which leads to the death of the cell. Apoptosis results in the death of damaged cells and protects the organism from potentially harmful genetic changes. Inhibition of apoptosis by abnormal expression of an oncogene or loss of a tumor suppressor gene can be closely associated with malignancy. As cells progress from a non-transformed state, through a pre-malignant state to a fully transformed state, the cells lose their ability to undergo apoptosis. Apoptosis is also inhibited by some viral infections.

Discovery of molecules which interfere with or inhibit cellular redox systems satisfies a need in the art by providing new diagnostic or therapeutic compositions useful in the detection, prevention, and treatment of diseases related to abnormal cellular activity (i.e., hyperproliferation or apoptosis).

SUMMARY OF THE INVENTION

Proteins and enzymes involved in cellular function provide an attractive site for the development of therapies and diagnostic tools for diseases associated with abnormal cellular function. These agents may serve as therapeutics themselves, or they may increase the efficacy of other therapeutic agents.

The present invention pertains to asymmetric disulfides and focuses on the interaction of these disulfides with cellular signaling pathways having points of redox control. Asymmetric disulfides that inhibit or interfere with cellular redox function have strong potential applications as therapeutic agents, diagnostic tools, chemopreventative agents and chemotherapeutic agents.

The present invention also relates to methods of using asymmetric disulfides for therapeutic and prophylactic treatment of a mammalian host, preferably a human. The disulfides of the present invention may be administered alone or in combination with other therapeutic agents (e.g. other anti-cancer drugs).

The present invention also relates to a composition comprised of an asymmetric disulfide and a pharmaceutically acceptable carrier of said asymmetric disulfide wherein said composition is useful in treating disease. It is preferable that the disulfides of the present invention also prevent the inhibition of apoptosis. The asymmetric disulfides preferably inhibit or interfere with thioredoxin redox system, and more preferably, the disulfides inhibit thioredoxin reductase or thioredoxin. The asymmetric disulfide and pharmaceutically acceptable carrier are preferably formulated or administered in a therapeutically effective amount. The therapeutically effective amount is preferably in a range from about 0.05 mg/kg/day to about 5,000 mg/kg/day, more preferably in a range from about 0.5 mg/kg/day to about 500 mg/kg/day, more preferably in a range of about 1 mg/kg/day to about 50 mg/kg/day, and more preferably yet, the therapeutically effective amount is in a range from about 2 mg/kg/day to about 20 mg/kg/day, and most preferably the therapeutically effective amount is in a range from about 5 mg/kg/day to about 10 mg/kg/day.

The present invention can also be described as a composition for treating a disease wherein the composition is comprised of an asymmetric disulfide in a sufficient dose to be effective in treating said disease. The disease is preferably related to redox function and more preferably related to abnormal cellular proliferation and/or abnormal apoptosis. The disease is preferably selected from the group consisting of cancer, reperfusion injury following ischemia, hepatitis, amyotrophic lateral sclerosis (ALS), neurodegenerative diseases, Alzheimer's diseases, Autoimmune disease, Sjogren's syndrome, Lupus, rheumatoid arthritis, HIV, Hermansky-Pudlack syndrome, retinal oxidative damage, retinopathy, skin hyperplasia, aging, ultraviolet damage, wound healing, Crohns' disease, ulcerative colitis, angiogenesis, uterine disorders, adult respiratory distress syndrome (ARDS), lung disorders, viral and other infections such as herpes virus, pox virus and adenovirus infections, inflammatory conditions, autoimmune diseases such as, systemic lupus erythematosus, psoriasis, inflammatory bowel disease, autoimmune diabetes, immune mediated glomerular nephritis, hyperproliferative diseases such as fibrosis, psoriasis and mycosis fungocides.

This invention also relates to a method of inhibiting growth in a cell, the method being comprised of contacting the cell with an effective amount of an asymmetric disulfide. It is preferable that the asymmetric disulfide be an inhibitor of a thioredoxin/thioredoxin reductase redox system, and even more preferable that the asymmetric disulfide prevents inhibition of apoptosis. The growth in a cell is inhibited by an effective amount of disulfide, and may be additive to the known effectiveness of other active inhibitors.

Another aspect of the present invention is a method of inhibiting tumor growth in vivo comprised of administering an effective amount of an asymmetric disulfide. The method of inhibiting tumor growth involves administering the disulfide in therapeutically effective amounts as described above, and preferably includes mixing the asymmetric disulfide with pharmaceutical acceptable carrier and/or other therapeutic agent.

The present invention can also be described as being drawn to asymmetric disulfides and their formulation in compositions, as well as methods of their use to treat various diseased states. It is preferable in the asymmetrical disulfides of the present invention have respective R groups of divergent functionality. Preferably in the general formula $R_1$—S—S—$R_2$ one of $R_1$ or $R_2$ is a good leaving group and the respective other is a poor leaving group. Examples of good leaving groups are compounds which contain electron withdrawing groups or groups which delocalize the electrons of the functional groups (i.e., aromatic and imidazlyl groups). It is preferable that the aromatic groups of the present invention include heteroatoms such as oxygen, nitrogen, and sulfur. Poor leaving groups do not generally have such electron withdrawing characteristics or delocalized electrons. Thus, they do not form substantially stable species when or if they are cleared from the molecule. An example of a poor leaving group is an unsubstituted alkane or alkyl group. The asymmetrical disulfides of the present invention are particularly useful to treat cancers, more particularly, cancers such as myeloma, cervical, lung, gastric, colon, renal, prostate, and breast cancers.

Finally, the present invention relates to a method of treating a diseased state by administering a therapeutically effective amount of an asymmetric disulfide having a predetermined $IC_{50}$ TR/Trx value, toxicity value, or hydrophilicity as described herein. The asymmetric disulfide preferably has $IC_{50}$ TR/Trx of less than 150 µg/ml, more preferably, less than 100 µg/ml, and even more preferably, less than 50 µg/ml.

BRIEF DESCRIPTION OF THE DRAWINGS

The features, aspects and advantages of the present invention can be better understood with regard to the following description, appended claims, by referring to the accompanying drawings, where:

DETAILED DESCRIPTION OF THE INVENTION

Figure 1:
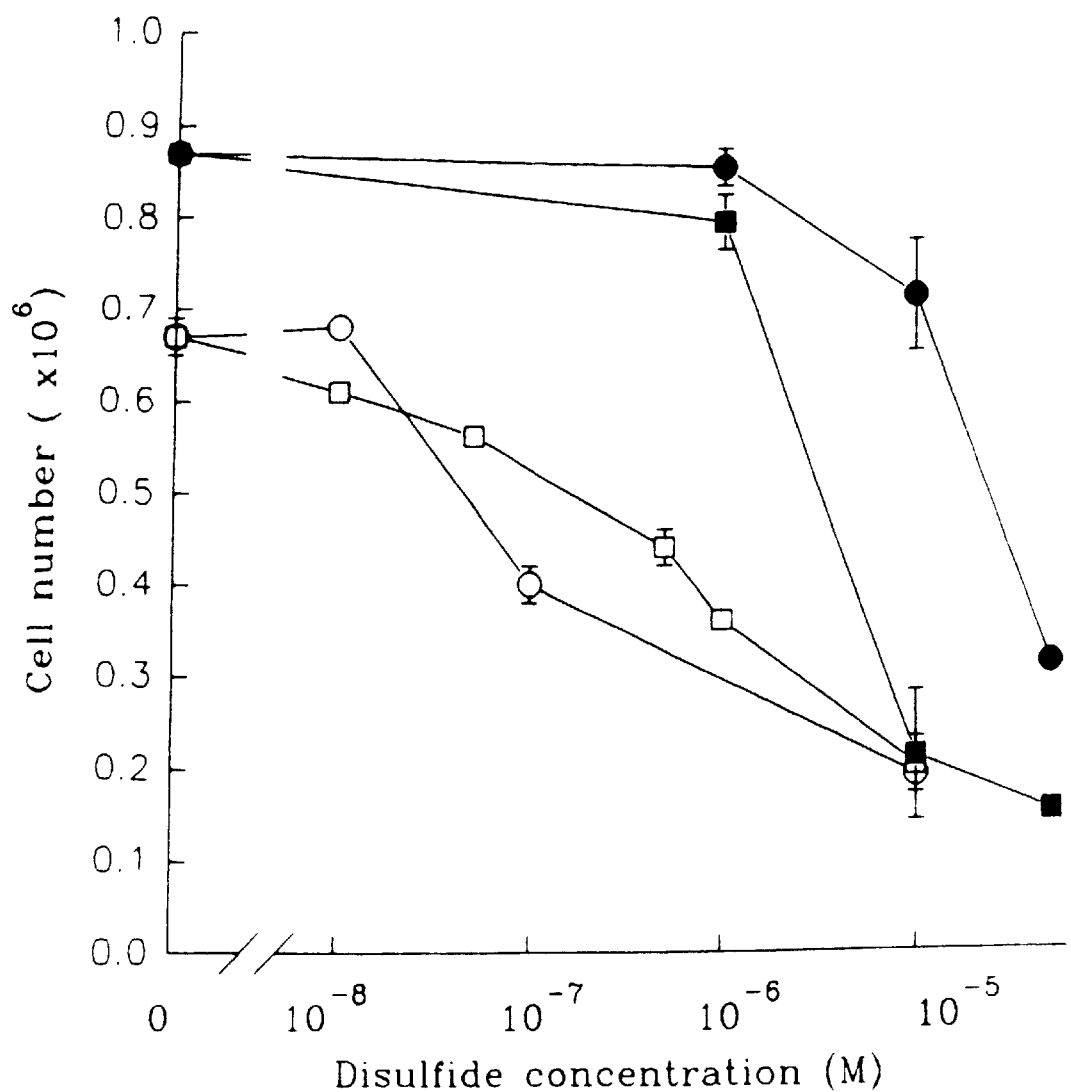
FIG. 1 illustrates inhibition of thioredoxin and serum dependent growth of MCF-7 human breast cancer cells by asymmetric disulfides III-2 (●,○)and IV-2 (■,□)

The present invention relates generally to asymmetric disulfides. More specifically, the present invention relates to compounds or mixtures of compounds which include an asymmetric disulfide or biological equivalent thereof which interacts, interferes, inhibits, or competes with redox systems, particularly redox systems involving proteins having cysteine residues, and more particularly to redox systems involving thioredoxin and/or thioredoxin reductase. The asymmetric disulfides of the present invention may be used alone or in combination with other therapeutic agents or therapeutic methods. Combination therapy (i.e., chemotherapy) using two or more therapeutic drugs to treat malignant tumors in humans is specifically contemplated herein. For cancer, therapeutic or anti-cancer drugs may include anti-metabolites, alkylating agents, antibiotics, tubulant binders, etc. Combinations of drugs are administered in an attempt to obtain a synergistic cytotoxic effect on most cancers, e.g., carcinomas, melanomas, lymphomas and sarcomas, and to reduce or eliminate emergence of drug-resistant cells and to reduce side effects to each drug.

As used herein, the term asymmetric disulfide means any compound having a sulfur-sulfur linkage which is not a mirror image of itself when split down the sulfur-sulfur. When speaking of a particular asymmetric disulfide, the term includes all biochemical equivalents (i.e. salts, precursors, and basic form) of the particular asymmetric disulfide being referenced (i.e., reference to n-butyl imadazolyl disulfide includes the salt thereof). This term specifically includes disulfides having the general formula of $R_1$—S—S—$R_2$ as well as (bis)disulfides having the general formula of $R_1$—S—S—Y—S—S—$R_2$ wherein $R_1$, $R_2$, and Y may be any chemical substituent, but is preferably selected from the group consisting of imidazoles, thiadiazolyls, thiazolyls, benzimidazolyls, purinyls, phenyl, benzyl, phenylethyl, pyridine, pyrimidine, benzoxazole, benzthiazolyls, alkyl, cycloalkyl, hydroxylalkyl, carboxyalkyl, haloalkyl, and cycloalkanone.

When the term asymmetric disulfide is used it means that the groups on either side of a disulfide linkage are not the same. In the case of disulfides having the formula R—S—S—R this asymmetric relation may be represented by $R_1$—S—S—$R_2$. In the case of (bis)disulfide compounds although $R_1$ and $R_2$ may not be different, and the overall compound may be "symmetrical" around the center of the formula, that is, in the formula $R_1$—S—S—Y—S—S—$R_2$, $R_1$ and $R_2$ may be the same group, the term asymmetrical as used herein refers to the fact that when either sulfur-sulfur linkage is split down the middle, the disulfides are asymmetrical (i.e. R—S—S—Y—S—})are not equivalent. By this definition and as used herein all (bis)disulfide compositions are asymmetrical.

The preferred asymmetric disulfides of the present invention include imidazolyl disulfide, thiadiazolyl disulfide, mercaptothiadiazolyl disulfide, thiazolyl disulfide, phenyl disulfide, benzyl disulfide, phenylethyl disulfide, nicotinic acid disulfide, pyrimidine disulfide, benzoxazolyl disulfide, benzothiazolyl disulfide, benzimidazolyl disulfide, purinyl disulfide, cycloalkyl disulfide, captopril disulfide, and menthone disulfide.

As used herein, the term "prophylactic or therapeutic" treatment refers to the administration to the host or subject of asymmetric disulfides or after onset of the biological damage. If the asymmetric disulfides and/or biological agent (s) are administered prior to exposure to the agent causing the biological damage or to prevent occurrence of the disease, the treatment is prophylactic (i.e., it protects the host against the damage), whereas if it is administered after exposure to the agent causing the damage, the treatment is therapeutic (i.e., it alleviates the existing disease or damage).

As used herein "to mix", "mixing", or "mixture(s)" means any mixing of an asymmetric disulfide with another agent or a pharmaceutically acceptable carrier of said asymmetric disulfide: 1) prior to administration ("in viuo"); 2) by simultaneous and/or consecutive but separate intravenous lines of disulfide and other agent or carrier to cause "in vivo mixing"; and 3) the administration of one or the other of disulfide and agent or carrier consecutively, preferably within 48 hours of one or the other ("delayed in vivo mixing" or "saturation").

As used herein, the term "about" means plus or minus 10% of the number to which reference is being made. For example, about 10 grams means in the range of 9–11 grams.

As used herein, $IC_{50}$ refers to the concentration causing 50% inhibition in activity in the system being measured. For example, in the thioredoxin reductase/Trx insulin reduction assay, $IC_{50}$ is defined as that concentration of inhibitor which causes a 50% decrease in the reduction of insulin by thioredoxin reductase/thioredoxin. When referring to the particular system being analyzed $IC_{50}$ is typically followed by an abbreviation referring to that system (i.e., $IC_{50}$ TR/Trx for the above described thioredoxin redox system which is comprised of thioredoxin reductase and thioredoxin).

As used herein, $GI_{50}$ refers to that concentration of inhibitor which produces a mean 50% growth inhibition. Similar to $IC_{50}$, $GI_{50}$ normally designates the system being analyzed or the type of cell lines being tested. For example $GI_{50}$ (all tumors) as used herein refers to the mean growth inhibition in all 60 cell lines of the National Cancer Institute, while $GI_{50}$ (leukemias) refers to a mean 50% growth inhibitor for leukemia cell lines of the National Cancer Institute.

As used herein, the term "leaving group" refers to a stable species that can be dettached from a molecule during a reaction and "good leaving group" refers to those species that can be displaced by a nucleophillic attack on a sulfur of an asymmetric disulfide or a (bis)disulfide. Preferably, the good leaving group includes an electron withdrawing group such as a carbonyl or a group which provides for electron delocalization such as an aromatic group.

The pharmaceutical compositions utilized in this invention may be administered by any number of routes, including but not limited to, oral, intravenous, intramuscular, intra-arterial, intramedullary, intrathecal, intraventricular, transdermal, subcutaneous, intraperitoneal, intranasal, enteral, topical, sublingual, or rectal means. In addition to the active ingredients, the compositions may contain suitable pharmaceutically-acceptable carriers comprising excipients and auxiliaries which facilitate processing of the active compounds into preparations which can be used pharmaceutically. As used herein, the term "pharmaceutically acceptable carrier" refers to a carrier medium which does not interfere with the effectiveness of the biological activity of the active ingredients and which is not toxic to the hosts to which it is administered.

As used herein, the term "pharmacologically effective amounts" refers to the amount of the referenced component which results in an increase survival of the host, or results in a desirable clinical outcome. The "therapeutic index" is defined for purposes herein in terms of efficacy (e.g., extent of tumor or infection reduction or other cure) and/or in terms of toxicity to the host. For non-human hosts, if the efficacy increases at least 50% over the efficacy using an excipient control (e.g., phosphate buffered saline) and the ratio of mean body weight at the end of the evaluation period for efficacy response to mean body weight at the start of treatment is at least 0.90 (i.e., no greater than 10% body weight loss), the therapeutic index has increased. [The ratio of mean body weights indicates the extent of toxicity, with a value of 1 indicating no toxicity.] For non-human hosts being treated for cancer, the extent of efficacy achieved may be measured by the ratio of mean tumor volume at the end of the evaluation period to mean tumor volume at the start of treatment. A reduction in the ratio of at least 50% of treated over excipient control indicates increased efficacy. The most preferred doses, schedules, and types of therapeutic agents are those that achieve a mean tumor volume ratio of between 0 and 5, with a value of 0 being optimum and indicating a cure. For human hosts, if the efficacy increases at least 50% upon treatment with the therapeutic agents and the toxicity is acceptable (i.e., no more than fever, chills, and/or general malaise) the therapeutic index has increased. For human hosts being treated for cancer, the extent of efficacy is generally ascertained in the clinic by measuring the perpendicular diameters of the products of all measured disease. The effect of the doses may diminish with time. For humans the dose may be repeated for months or even years.

A "therapeutically effective dose" refers to that amount of active ingredient, for example, asymmetric disulfide compound, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The therapeutic index can be defined as the dose ratio between therapeutic and toxic effects (the ratio $LC_{50}/ED_{50}$). Pharmaceutical compositions which exhibit large therapeutic indices are preferred.

As used herein, the term "biological damage" refers to any damage to cellular components, body tissue or other body parts or functions sustained by the host, as a result of abnormal redox in the host (i.e. abnormal cellular proliferation).

The term "cancer" as used herein refers to any neoplastic disorder, including such cellular disorders for example, renal cell cancer, Kaposi's sarcoma, chronic leukemia, breast cancer, sarcoma, ovarian carcinoma, rectal cancer, prostate cancer, throat cancer, melanoma, colon cancer, bladder cancer, mastocytoma, lung cancer and gastrointestinal or stomach cancer. Preferably, the cancer is colon cancer, breast cancer and gasteric cancer, melanoma, renal cell cancer, sarcoma, lung cancer, adenocarcinoma, prostate or breast cancer. Even more preferably colon, breast, lung, gastric and prostate cancer.

The thioredoxin redox couple (TR/Trx) is a ubiquitous redox system found in both prokaryotic and eukaryotic cells. The thioredoxin system is comprised primarily of two elements: thioredoxin and thioredoxin reductase. Thioredoxin reductase is a NADPH-dependent selenium containing flavoprotein that catalyzes the reduction of thioredoxin. $E.\ coli$ thioredoxin reductase is a 70 kDa homodimer. The active site cysteine residues, Cys-135 and Cys-138, receive electrons from $FADH_2$ and transfer them to the active cysteine bond of thioredoxin. During reduction, thioredoxin reductase undergoes a conformation change which protects the reduced active site cysteines from the aqueous phase, preventing spontaneous oxidation. Upon binding of oxidized thioredoxin to the active site, thioredoxin reductase undergoes a conformation change to expose the active site cysteines, allowing reduction of thioredoxin's cystine bond. Thioredoxin reductase of higher organisms is a 116–129 kDa homodimer. Human placental thioredoxin reductase has been cloned. The active site of human thioredoxin reductase has a conserved Cys-Val-Asn-Val-Gly-Cys amino acid sequence in the FAD binding domain and a C-terminal Gly-Cys-CysSe-Gly amino acid sequence. This is unexpected due to the normal DNA stop codon TGA coding for selenocysteine (CysSe) because of a 3'-untranslated signal stem loop signal sequence. The CysSe residue is critical for the activity of human thioredoxin reductase. Studies have shown that the CysSe residue can reduce bacterial thioredoxin, albeit at a decreased rate, compared to human thioredoxin reductase. A gene for human thioredoxin reductase is located at chromosomal position 12q23–q24.1.

Thioredoxins are a class of low molecular weight redox proteins characterized by a highly conserved -Cys-Gly-Pro-Cys-Lys active site. The cysteine residues at the active site of thioredoxin undergo reversible oxidation-reduction reactions catalyzed by thioredoxin reductase. The human thioredoxin gene has been mapped to 9q31. Analysis of genomic clones of thioredoxin have found that the entire gene spans 13 kb and is comprised of 5 exons. X-ray crystal studies have identified a highly conserved 12 amino acid hydrophobic surface on vertebrate, but not bacterial, thioredoxins, accounting for 10% of the solvent accessible surface of the protein.

It has been shown that the deduced amino acid sequence of thioredoxin is identical to that of a previously known protein called eosinophil cytotoxicity stimulating factor, or adult T-cell leukemia-derived factor (ADF). Human thioredoxin has a 27% amino acid identity to $E.\ coli$ thioredoxin, and contains in addition to the catalytic site cysteine residues other cysteine residues that are not found in bacterial thioredoxin. As discussed below, very high levels of thioredoxin have been seen in some human tumor cell lines, primarily human tumors. These cysteine residues appear to give human thioredoxin unique growth promoting activity.

Thioredoxin exerts specific redox control over a number of transcription factors to modulate their DNA binding and, thus, to regulate gene transcription. Transcription factors regulated by thioredoxin include NF-kB, TFIIIC, BZLF1 and the glucocorticoid receptor. The transcription factor activator protein-1 (AP-1) (Fos/Jun heterodimer) is subject to redox control by the nuclear redox factor Ref-1/HAP-1 which, in turn, is reduced by thioredoxin. The importance of redox regulation of transcription factor activity is illustrated by the oncogene v-fos where a point mutation converts $Cys^{154}$ to a serine residue resulting in constitutive activation and DNA binding of the Jun protein.

Human recombinant thioredoxin has been shown to stimulate the proliferation of human epithelial cancer cells. This appears to be due to thioredoxin's ability to enhance the activity of endogenously produced growth factors, either by acting on the factors themselves, or by affecting the factors' interaction with its cell surface receptor. For example, thioredoxin at nanomolar levels produces a $10^3$ fold enhancement of the growth stimulating activity of interleukin-2 and a $10^2$ fold enhancement of the activity of basic-fibroblast growth factor with MCF-7 human breast cancer cells. Mutant redox-inactive forms of thioredoxin lacking the active site cysteine residues and $E.\ coli$ thioredoxin are devoid of growth stimulating activity. It has been found that exogenously added thioredoxin stimulates mouse fibroblasts and a number of human solid tumor cells lines. Thioredoxin stimulates cell growth up to 90% as effectively as 10% fetal bovine serum stimulation. This is a characteristic exhibited by few other growth factors. One exception to this appears to be HepG2 cells whose proliferation is stimulated by thioredoxin in serum free medium, but is inhibited in the presence of 0.5% serum.

Mechanistically, thioredoxin does not appear to stimulate cell growth along classical lines by acting on a specific cell-surface receptor. There was no evidence for saturable binding of $^{125}I$-thioredoxin to the surface of MCF-7 breast cancer cells and there was minimal uptake of the $^{125}I$-thioredoxin into the cells. Instead, thioredoxin appears to exert its cell growth stimulating effect by sensitizing cells to growth factors produced by the cell itself. Replacing medium each day with fresh medium and thioredoxin reductase completely abolishes the increase in cell proliferation. Such a process presumably removes the factors secreted by cells that are necessary for thioredoxin-induced cell growth.

The $EC_{50}$ for thioredoxin growth stimulation in MCF-7 breast cancer cells is 350 nM, which is considerably higher than the 4–18 nM concentration of thioredoxin found in serum. Higher thioredoxin concentrations exist in tissues, 1 to 10 $\mu M$, which if released extracellularly might stimulate cell proliferation. Thioredoxin protein levels are elevated in a variety of human primary tumors including human cervical neoplastic squamous epithelial cells, gastric carcinoma, and hepatocellular carcinoma. It has been found that a significant number of human primary lung and colon cancers have increased thioredoxin mRNA compared to normal tissue. In humans, primary gastric carcinoma increased levels of thioredoxin are associated with aggressive tumor growth measured by high levels of proliferation antigen and low levels of apoptosis. NIH 3T3 cells stably transfected with thioredoxin cDNA show an increase in growth rate, while MCF-7 breast cancer cells transfected with cDNA for the redox inactive C32S/C35S mutant thioredoxin will no longer form colonies in soft agar. These results suggest that increased thioredoxin gene expression could contribute to the increased growth rate and transformed phenotype of some human tumors. Mouse NIH 3T3 cells and MCF-7 human breast cancer cells are transfected with cDNA for wild-type human thioredoxin or the redox-inactive mutant thioredoxin and immunodeficient mice. Thioredoxin transfected MCF-7 cells formed tumors, as did vector-alone transfected cells, but tumor formation by redox-inactive thioredoxin transfected MCF-7 cells was completely inhibited.

Thioredoxin has also been identified as a component in the early pregnancy factor (EPF) system, which is a complex array of factors present in the sera of pregnant mammals. The binding of lymphocytes to red blood cells (i.e., rosette bud formation) by EPF occurs during the initial onset of pregnancy. Several proteins of the EPF complex may act synergistically, or in combination. A mutagenesis study of human thioredoxin showed that the redox active, catalytic site Cys-32 and Cys-35 residues were not essential for this function, but that Cys-73 was.

In addition to its involvement in cellular proliferation, the TR/Trx system also appears to be involved or associated with apoptosis. Apoptosis has been associated with normal cellular behavior. There is now considerable evidence that an increase in reactive oxygen species constitutes an intracellular signal that can lead to apoptosis. Apoptosis can be induced in a number of cell systems by $H_2O_2$, reactive oxygen species generated by the redox cycling of quinones and radiation. It appears that c-myc, which is essential for apoptosis in many systems, is induced by $H_2O_2$ and reactive oxygen species. Hypoxia and antioxidants inhibit apoptosis induced by these treatments. Thioredoxin protects lymphoma cells against TNF-α-mediated cell killing. The survival of embryonic mouse neurons is enhanced by thioredoxin, as well as by 2-mercaptoethanol and N-acetylcysteine. In the same studies, U251 astrocytoma cells were seen to produce increased levels of thioredoxin in response to $H_2O_2$ treatment. Elevated thioredoxin levels have also been observed in glial cells of the gerbil brain during reperfusion after ischaemia. Thus, thioredoxin secreted by glial cells may protect neurons, in vivo, from oxidative stress-induced cell death.

It appears that a decrease in antioxidant enzymes could lead to an increase in cellular reactive oxygen species responsible for signaling apoptosis. Transfection of lymphoid cancer cells with thioredoxin cDNA blocks apoptosis induced by a variety of agents, including, etoposide, staurosporine, thapsigargin and glucocorticoids. This is similar to the pattern seen with the antiapoptotic oncogene bcl-2. When inoculated into scid mice, the trx transfected cells form tumors that grow faster than wild type or bcl-2 transfected cell tumors (due to a decreased spontaneous rate of apoptosis) and they are resistant to growth inhibition by treatment with dexamethasone.

In addition to its growth enhancing effects, thioredoxin appears to cause tumors to be resistant to anti-cancer drugs. Thus, TR/Trx system appears to play an important role in human cancer.

Many diseases appear to be associated with weakened antioxidant defenses and oxidative stress. It should be emphasized that the increase in reactive oxygen species that follows a decrease in antioxidant enzymes is, most likely, a signaling event and not an effector mechanism for apoptosis. That is, oxygen radicals are not directly responsible for the DNA degradation and membrane damage seen during the final common pathway of apoptosis as has been proposed by some investigators. Furthermore, reactive oxygen species are probably only one of a number of signaling events that can initiate apoptosis. It is known, for example, that hypoxia does not inhibit apoptosis caused by staurosporine, by a nonspecific PKC inhibitor, by the FAS receptor, by withdrawal of IL-3 from IL-3-dependent cells or by the topoisomerase inhibitor camptothecin. The endogenous formation of reactive oxygen species could however, be a constitutive factor that tends to drive cells to apoptosis even in the absence of exogenous stimuli. Such a model of apoptosis is consistent with the view that the default state of cells is to die by programmed cell death unless kept alive by specific signals from other cells in the form of growth factors and anti-apoptotic agents. It may be that cancerous cells deliver their own survival signals, thus, becoming resistant to both intrinsic and induced apoptosis.

There are other disease states where weakened antioxidant defenses and oxidant stress are associated with inappropriate cell death. Genetic studies of individuals with amyotrophic lateral sclerosis (ALS) have identified mutations in the gene coding for Cu,ZnSOD. These mutations result in decreased enzyme activity, which may contribute to the observed pathology of motor neuron death. $CD4^+$ cells and lymph nodes from AIDS patients have decreased levels of GSH and thioredoxin, respectively. Catalase, MnSOD and glutathione peroxidase activities drop in T cell lines grown in vitro, after infection with the HIV virus. Alpha-amyloid is a neurotoxic peptide that aggregates in the brain of Alzheimer's patients and has been found to generate free radical peptides. This has led to the hypothesis that oxidative stress, specifically, membrane damage mediated by the α-amyloid-derived radicals, leads to the neurodegeneration seen with Alzheimer's disease. Two apoptosis-linked genes have been isolated that were able to inhibit T cell receptor-induced cell death. ALG-2 which codes for a $Ca^{2+}$-binding protein may regulate signals along the death pathway, and ALG-3, a partial complementary DNA that is homologous to the familial Alzheimer's disease gene STM2, may link that cell death pathway to Alzheimer's disease.

Thioredoxin mRNA is increased in some cases up to 100-fold compared to corresponding normal tissue, in almost half of the human primary lung, colon and gastric tumors examined. Thioredoxin levels have also been reported to be increased in human cervical neoplastic squamous epithelial cells and hepatocellular carcinoma. Thioredoxin activity is increased almost two-fold in human colon cancer compared to normal colonic mucosa. Thioredoxin is known to be excreted from cells by a leaderless secretory pathway so that overexpression of thioredoxin could lead to production of an autocrine growth factor for some human cancers.

Over-expression or under-expression of either thioredoxin reductase or thioredoxin appear to play a role in the development of disease. Increased expression of thioredoxin is associated with increased growth leukemia and lymphoma cells, autoimmune disease such as Sjogren's syndrome, rheumatoid arthritis, Lupus, cancer and AIDS. A deficiency of thioredoxin reductase is associated with Hermansky-Pudlack syndrome.

There is a need for drugs which will inhibit the activity of the thioredoxin system and consequently decrease tumor cell growth and prevent aggressive cancer disease. The asymmetric disulfides of the present invention provide the ability to alter cellular redox in such a fashion as to manipulate the growth regulating proteins associated with undesirable health conditions.

The materials and methods of the present invention are as follows: Enzymes: Thioredoxin reductase, specific activity 43.6 μmole NADPH reduced/min/mg protein at 21° C., was purified from human placenta as previously described (Oblong et al., 1993). Glutathione reductase, specific activity 141.2 μmole NADPH reduced/min/mg protein at 21° C., was purified from aged human red blood cells (Colmon & Black, 1965). Human recombinant thioredoxin was expressed in E. coli and purified as previously described (Gasdaska et al., 1994). The thioredoxin was stored at −20° C. with 5 mM dithiothreitol which was removed before use with a desalting column (PD10, Pharmacia, Uppsala, Sweden).

The interaction of a series of asymmetric disulfide compounds showing particular application to the thioredoxin reductase/(TR) thioredoxin (thioredoxin) redox system are described herein. Disulfides III-2 (n-butyl 2-imidazolyl disulfide—(C-1)) and VI-2 (ethyl 2-imidazolyl disulfide (A-1)) were substrates for reduction by thioredoxin reductase with Km values of 43 and 48 μM. Disulfides IV-2 (1-methylpropyl 2-imidazolyl disulfide (F-1)) and DLK-36 (benzyl 2-imidazolyl disulfide (I-1)) were competitive inhibitors of the reduction of thioredoxin by thioredoxin reductase with Ki values of 31 μM. None of these disulfides were substantial substrates for reduction by human glutathione reductase. The disulfides caused reversible thioalkylation of thioredoxin at the redox catalytic site as shown by the fact that there was no initial measurable reaction of the mutant thioredoxin where both the catalytic site $Cys^{32}$ and $Cys^{35}$ residues were replaced by Serine. In addition, the disulfides caused a slower irreversible inactivation of thioredoxin as a substrate for reduction by thioredoxin reductase, with half lives for III-2 of 30 min, for IV-2 of 4 hr and for IX-2 (t-butyl 2-imidazolyl disulfide (Q-1)) of 24 hr. This irreversible inactivation of thioredoxin occurred at concentrations of the disulfides an order of magnitude below those that inhibited thioredoxin reductase, and involved the $Cys^{73}$ of thioredoxin which is outside the conserved redox catalytic site, as shown by the resistance to inactivation of a mutant thioredoxin where $Cys^{73}$ was replaced by Ser. Electrophoretic analysis (not shown) and mass spectral analyses (i.e., FIGS. 3A, 3B and 3C) of the products of the reaction between the disulfides and thioredoxin, show modification of 1 to 3 cys residues of the protein occurs in a concentration dependent fashion. The disulfides inhibited the thioredoxin dependent proliferation of MCF-7 breast cancer cells with $IC_{50}$ values for III-2 and IV-2 of 0.2 and 1.2 μM, respectively. While not wishing to be bound by theory, the results appear to illustrate that although the catalytic sites of thioredoxin reductase and thioredoxin are reversibly inhibited by the asymmetric disulfide, specifically 2-imidazolyl disulfides, it is the irreversible thioalkylation of $Cys^{73}$ of thioredoxin by the disulfides that most probably accounts for the inhibition of thioredoxin dependent cell growth by the disulfides.

Not only do the asymmetric disulfides studied herein inhibit the growth of cancer cells in vitro, they show in vivo anti-tumor activity against human tumor xenografts in scid mice.

Asymmetrical 2-imidazolyl disulfides which were used as a basis for further development and identified below in Table 1. In Table I, NADPH oxidation by thioredoxin reductase was measured spectrophotometrically as described with either the disulfide as the electron acceptor (substrate) or with thioredoxin and insulin as the final electron acceptor and the disulfide as inhibitors. The reactions were initiated by the addition of NADPH. Km and Ki values were calculated from Lineweaver-Burk plots of the data.

TABLE 1

Effects of 2-imidazolyl Disulfides On Human Thioredoxin Activity

| Compound | R | Type | Km (μM) | Ki |
|---|---|---|---|---|
| ethyl 2-imidazolyl disulfide (VI-2) | —$CH_2CH_3$ | substrate | 48.1 | — |
| n-butyl 2-imidazolyl disulfide (III-2) | —$(CH_2)_3CH_3$ | substrate | 43.1 | — |
| 1-methylpropyl 2-imidazolyl disulfide (IV-2) | —$CH(CH_3)CH_2CH_3$ | inhibitor | — | 30.8 |
| t-butyl 2-imidazolyl disulfide (IX-2) | —$C(CH_3)_3$ | non-reactive | — | — |
| benzyl 2-imidazolyl disulfide (DLK-36) | —$CH_2C_6H_5$ | inhibitor | — | 30.9 |

The compounds of Table 1 were synthesized by a method described previously and recrystallized prior to use. Stock solutions of the disulfides were prepared at 10 mM in ethanol and diluted in aqueous media just prior to use. N-ethylmaleimide (NEM), diamide, and DTT were obtained from Sigma Chemical Co. (St. Louis, Mo.). All other chemicals used were of reagent grade. Human placental thioredoxin reductase (specific activity 33.3 μmole NADPH reduced/min/mg at room temperature) was purified as previously described and human glutathione reductase (specific activity 141.2 μmole NADPH reduced/min/mg at room temperature) was purified from aged human red blood cells.

MCF-7 human breast cancer cells were obtained from the American Tissue Type Collection (Rockville, Md.). Cultures were maintained in Dulbecco's Modified Eagles' medium (DMEM) containing 10% fetal bovine serum (fbs) at 37° C. and 6% $CO_2$, and passaged at 75% confluence using 0.025% trypsin. The effect of the disulfides on cell proliferation was measured as previously described and incorporated herein by reference. Briefly, $10^5$ cells were plated in a 35 mm culture dish in the above medium and, after attachment for 24 hr, their growth was arrested by changing to DMEM with 0.5% fbs for 48 hr. The medium was then replaced with DMEM containing 10% fbs or 1 μM thioredoxin, with or without the disulfides. The cell number was measured 2 days later following detachment with 0.025% trypsin using a hemocytometer. All incubations were conducted in triplicate and results expressed as the concentration of disulfide that inhibited cell proliferation by 50% ($IC_{50}$).

The effects of the assymetric disulfides of Table I on the reduction of thioredoxin and C73S by thioredoxin reductase was measured spectrophotometrically by following the reduction of NADPH at 339 nm. The Km of disulfides that were substrates for thioredoxin reductase was measured using an incubation mixture that contained 2.8 μg/mL thioredoxin reductase, 100 mM HEPES buffer, pH 7.6, 5 mM EDTA and at least 6 concentrations of disulfide between 10 to 400 μM with the reaction initiated by the addition of 140 μM NADPH. For disulfides that were inhibitors of thioredoxin reductase the Ki was measured with at least 3 concentrations of disulfide using an incubation mixture that contained thioredoxin at 60 to 240 nM and 1 mg/mL bovine insulin as the final electron acceptor. In some studies the disulfides at 3.5 μM were preincubated for up to 24 hr at room temperature in air with 0.7 μM thioredoxin or C73S in 100 μM HEPES buffer, pH 7.6, and 5 mM EDTA, before measuring the reduction of the thioredoxin or C73S by thioredoxin reductase with 1 mg/ml bovine insulin as the final electron acceptor. The ability of the disulfides to act as substrates for glutathione reductase was measured by following the reduction of NADPH using an incubation mixture containing 0.15 µg/ml glutathione reductase, 140 µM NADPH, 100 mM HEPES buffer, pH 7.6, 5 mM EDTA and the disulfides at 500 µM. The ability of the disulfides to act as inhibitors of glutathione reductase was measured using oxidized glutathione, 50 µM, as the final electron acceptor. In both cases the reaction was initiated by the addition of NADPH. Thioredoxin or C32S/C35S, 2 µM, in 0.1 M sodium phosphate buffer, pH 7.4, was reacted with the disulfides at a concentration of 200 µM at room temperature. This direct reaction between thioredoxin and the disulfides was followed spectrophotometrically as the increase in absorbance at 252 nm due to release of 2-mercaptoimidazole. Initial reaction rates were measured in triplicate.

All studies involving mass spectrometry were performed using an ESI-TOF mass spectrometer. Samples were dissolved in 5 mM ammonium acetate pH 6.5 at a final concentration of $10^{-5}$M and were continuously infused into the ion source at a flow rate of 0.4 µL/min using a Harvard Model 11 syringe pump (Harvard Apparatus). The declustering voltage, which controls the kinetic energy of the ions in the instrument interface was set to 100 V, and the capillary temperature to 110°. Data were acquired in the positive mode and calibration was performed using the multiply charged ions produced by a separate injection of substance P dissolved in a mixture of water/methanol: 1/1 with 1% acetic acid. The samples (200 µL) were assembled in "waterbugs" and dialysed with 8000 MWCO membrane (Spectra/Por 7) against 10 mM $NH_4OAc$ pH 6.5 with six changes over 48 hr. Prior to mass analysis, the samples were diluted to a final concentration of 10 µM in 5 mM $NH_4OAc$, pH 6.5 (non-denaturing conditions) or in $H_2O$/MeOH: 1/1, 1% acetic acid (denaturing conditions). Reduction of the drug was achieved by addition of 10 µL 2-mercaptoethanol (2-ME; 100 mM in water) to 30 µL protein solution (in 10 mM $NH_4OAc$, pH 6.5). After 24 hr at 37° the mixtures were dialysed once using a 5000 MWCO filter (Millipore), diluted with water to $10^{-5}$M protein concentration and infused into the mass spectrometer.

The effects of the disulfides on the growth of human MCF-7 breast cancer cells is shown graphically in FIG. 1. Inhibition of thioredoxin and serum dependent growth of MCF-7 human breast cancer cells by imidazolyl disulfides III-2 (●,○)and IV-2 (■,□) are illustrated therein. The cells were growth arrested in medium with 0.5% serum for 48 hr at which time there were $0.2 \times 10^6$ cells. DMEM with 1 mM thioredoxin (open symbols) or 10% serum (filled symbols) was added and the increase in cell number over a 48 hr period was measured in the presence of various concentrations of the disulfides. Values are means±SEM. n=6. The $IC_{50}$s of III-2 and IV-2, respectively, with 10% fetal bovine serum were 35.0 mM and 3.2 µM, and in the presence of 1 µM thioredoxin the $IC_{50}$s were 0.2 µM and 1.2 µM, respectively.

As can be seen, disulfides III-2 and VI-2 were substrates for reduction by thioredoxin reductase. Disulfides IV-2 and DLK-36 were not identifiable substrates but rather were competitive inhibitors of the reduction of insulin by thioredoxin reductase and thioredoxin. None of the disulfides were identifiable substrates for reduction by human glutathione reductase nor did they inhibit the reduction of oxidized glutathione by glutathione reductase (results not shown).

Figure 2A:
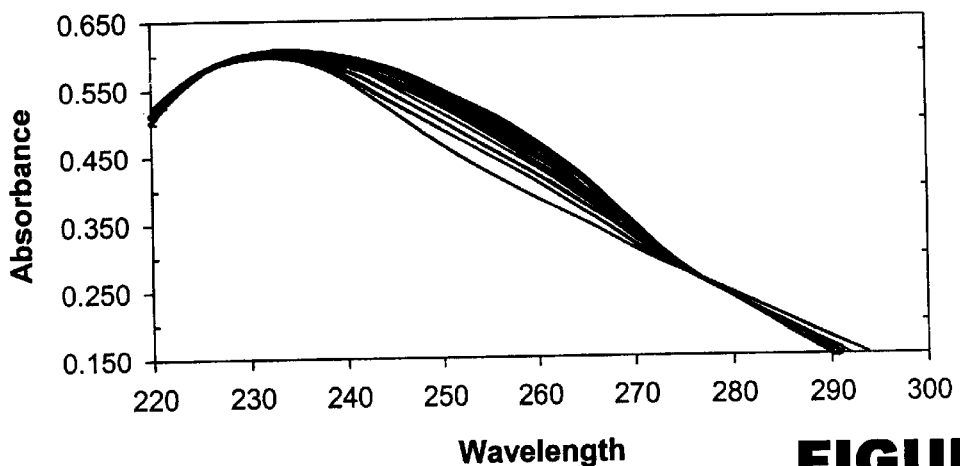
FIG. 2A illustrates sequential spectrophotometric scans at 2 sec intervals during the reaction between reduced thioredoxin (1 µM) and IV-2 (100 µM) at pH 7.4 and 25° C.
Figure 2B:
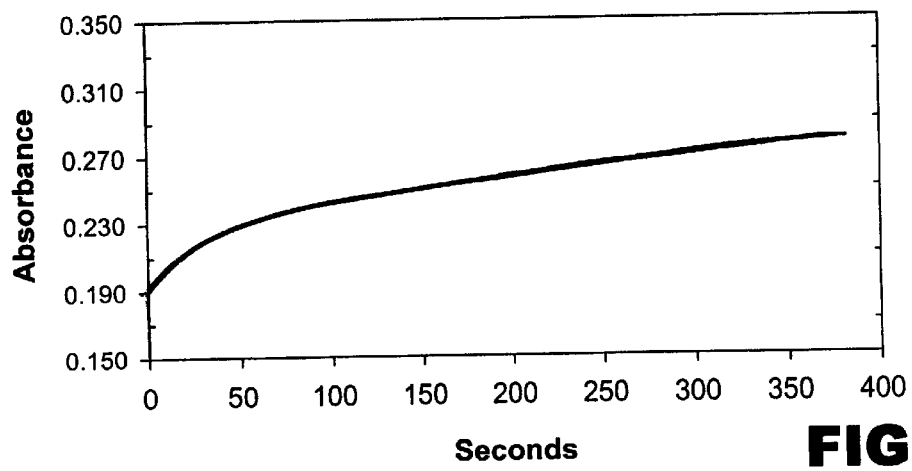
FIG. 2B illustrates time course of the reaction measured at 252 nm between IV-2 and reduced thioredoxin.
Figure 2C:
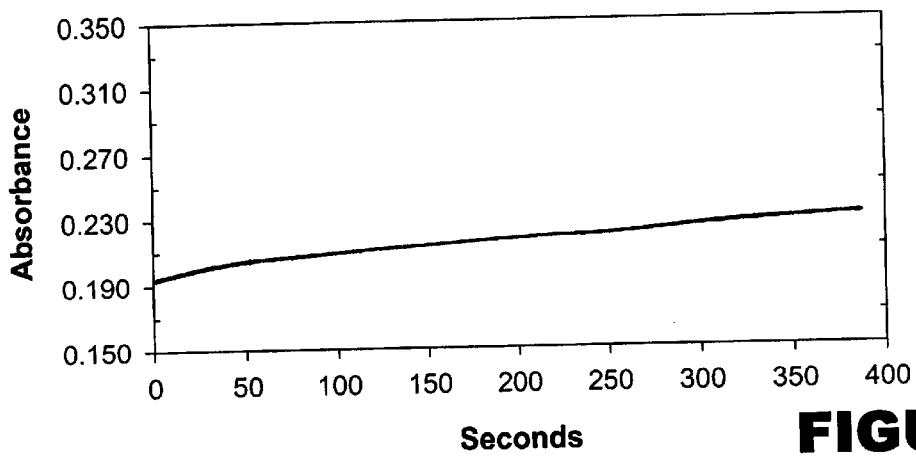
FIG. 2C illustrates time course of the reaction at 252 nm between IV-2 and oxidized thioredoxin.

Due to the fact that the disulfides inhibited thioredoxin-dependent cell growth at concentrations below those required to inhibit thioredoxin reductase, a direct effect of the disulfides on thioredoxin was looked for. The initial reaction between the disulfides and thioredoxin was measured spectrophotometrically (FIGS. 2A and 2B). The sharp isosbestic point obtained suggests a direct displacement reaction by the disulfides resulting in the release of 2-mercaptoimidazole (observed at 252 nm) and thioalkylation of thioredoxin producing the mixed disulfide between 1-methylpropylthiol and thioredoxin. The initial rate for reaction between thioredoxin and III-2 was $7.3 \times 10^{-7}$ $Ms^{-1}$, for IV-2 $2.8 \times 10^{-7}$ $Ms^{-1}$, for IX-2 $3.0 \times 10^{-9}$ and for DLK-36 $1.3 \times 10^{-6}$ $Ms^{-1}$. This is the order of reactivity which be predicted from the steric and electronic nature of the disulfides thioalkylating groups. No reaction was observed between the disulfides and either oxidized thioredoxin (FIG. 2C) or C32S/C35S active site mutant thioredoxin (not shown) suggesting that the initial reaction between the disulfides and thioredoxin occurs at the conserved active site Cys residues.

Treatment of thioredoxin with III-2 and IV-2 caused conversion to smaller molecular weight SDS bonds and the appearance of a new band at 23.3 kDa which corresponds to the thioredoxin homodimer. These changes were reversed upon treatment with the thiol reducing agent DTT. Treatment of thioredoxin with the thiol alkylating agent N-ethylmaleimide ("NEM") gave a single band at 11.4 kDa. This was not reversed upon reduction with DTT or 2-ME. Treatment of thioredoxin with diamide, a thiol oxidizing agent, gave bands at 10 kDa and 23.3 kDa. The bands at 10 kDa are attributed to oxidized species of the thioredoxin monomer, while that at 23.3 results from oxidation to the thioredoxin homodimer. In contrast, thioredoxin treated with either III-2 or IV-2 at 100 mM followed by 10 mM diamide did not exhibit increased dimerization and was the same as thioredoxin treated with disulfide alone. These results suggest that III-2 and IV-2 interact with a site on thioredoxin that inhibits dimerization. The interaction site is most likely to be $Cys^{73}$ which is essential for stabilization of the thioredoxin homodimer. Treatment of the Cys73S mutant thioredoxin with diamide or IX-2 did not result in homodimerization (results not shown). The relatively unreactive disulfide, IX-2, was found to cause predominantly dimerization of thioredoxin, although it was necessary to expose the thioredoxin to higher concentrations than for the other disulfides to produce the effect.

Mass spectral analyses of thioredoxin removed from 10 mM DTT and treated with III-2, IV-2 and IX-2 has provided data which demonstrates that a thiol/disulfides exchange reaction occurs producing the thioalkylated thioredoxin analogue. Thioredoxin removed from DTT was found to have a mass of 11,602±1.3 Da which corresponds to the calculated value for thioredoxin (11,607 Da fully reduced) having 2 disulfide bridges as might be expected for the protein in non-reducing conditions. The spectrum of reduced thioredoxin (25 µM) treated with 50 µM III-2 (FIG. 3A) illustrated that two major protein species were present, one with a mass of 11,690.8 Da and another with a mass of 11,868.8 Da. These correspond to a protein molecule modified with one thioalkyl residue [—$S(CH_2)_3CH_3$] and 3 thioalkyl residues. These modified proteins correspond to the major electrophoretic bands at 9.3 and 8.1 kDa. Treatment with 100 µM III-2 produced only one major species with a mass of 11868.6 Da (FIG. 3B) although a very small amount of protein was present with a mass of 11,690.4 Da. These results again correspond to the electrophoresis data which illustrates a major band at 8.1 kDa and a very faint band at 9.3 KDa.

Figure 3A:
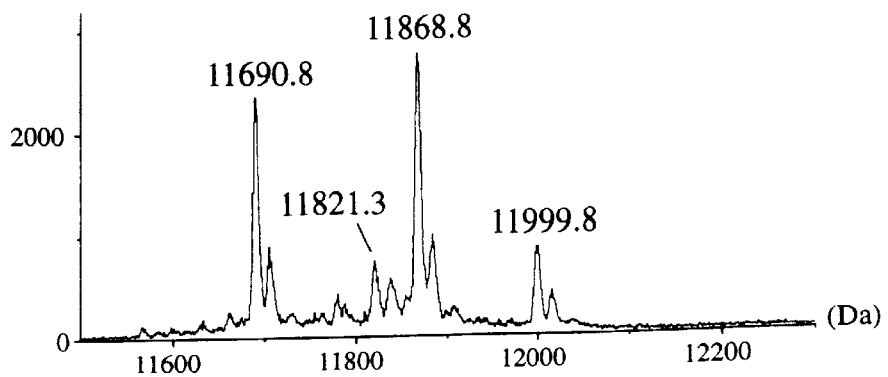
FIG. 3A illustrates the mass spectra of thioredoxin (20 µM) exposed to III-2 (50 µM)
Figure 3B:
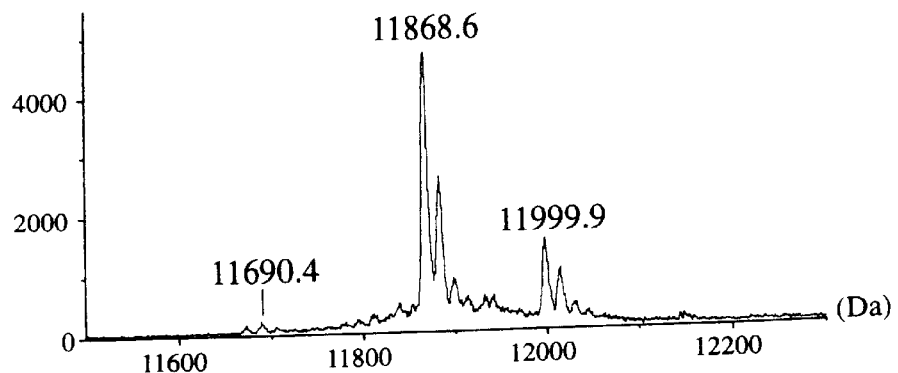
FIG. 3B illustrates the mass spectra of thioredoxin (20 µM) exposed to III-2 (100 µM)
Figure 3C:
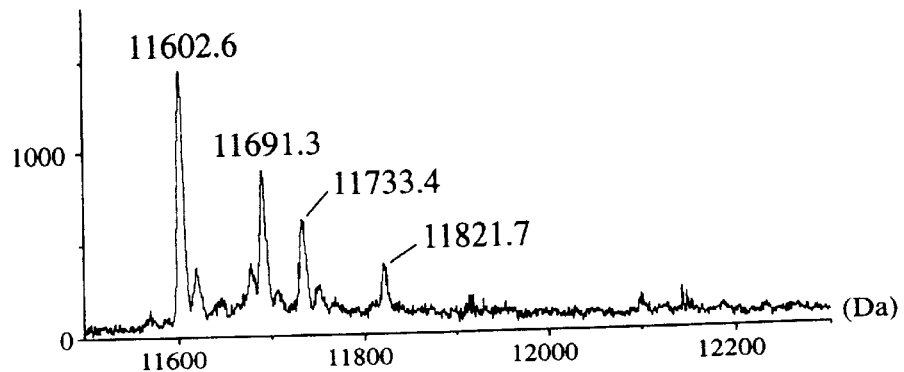
FIG. 3C illustrates the mass spectra of thioredoxin (20 µM) exposed to 100 mM 2-ME for 24 hr.

FIGS. 3A, 3B and 3C show mass spectra of thioredoxin (20 μM) exposed to 3A III-2 (50 μM); 3B III-2 (100 μM); and 3C of sample 3b exposed to 100 mM 2-ME for 24 hr. Unlabelled peaks to the right of the major ones (+16) may be oxidized protein. In FIG. 3A, the peaks at 11,821.3 and 11999.8 Da could be the +M protein with one and tree modified residues, respectively. In FIG. 3b, the singly modified +M protein peak would be too small to identify, but the peak at 11999.9 could be the +M protein with three modified residues. Treatment of the modified thioredoxin with 100 mM 2-ME for 24 hr at 37° resulted in one major species of mass 11,602 with smaller amounts of 11,692 Da (one modification), and the +M protein at 11,733.4 (11,602+131) and 11,821.7 (11,602 +131+89) (FIG. 3c). These results illustrate that reducing conditions removed the thioalkyl residues and again support the proposal that the modifications are the result of thioalkylation of the cys residues of thioredoxin. The data also suggest that two of the adducts are reduced more easily than the third, possibly the modified Cys 73.

Figure 4A:
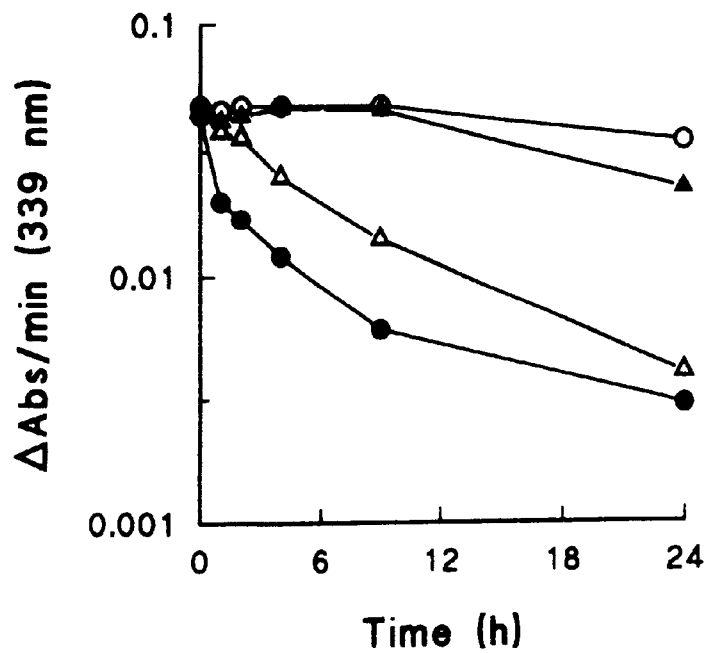
FIG. 4A illustrates effects of pre-incubation of thioredoxin and thioredoxin reductase with various disulfides with (○) control, (●) 111-2, (▽) IV-2 (▼), and (V) IX-2 (Q-1)
Figure 4B:
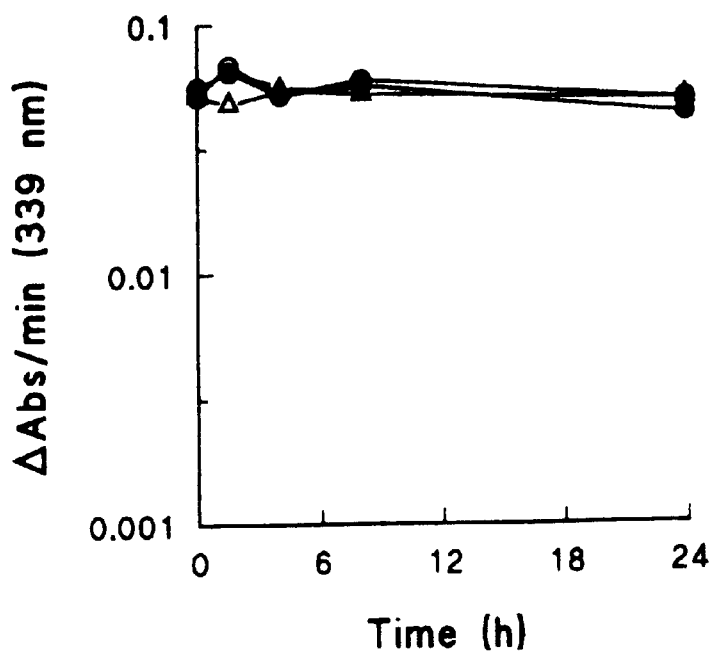
FIG. 4B illustrates effects of pre-incubation of thioredoxin and thioredoxin reductase with various disulfides with (○) control, (●) III-2 (C-1), (▽) IV-2 (F-1), and (▼) IX-2 (Q-1)

FIGS. 4A and 4B illustrate the effects of preincubation of thioredoxin and thioredoxin reductase with the disulfides on activity. The symbols in FIGS. 4A and 4B represent (○) control; (●) III-2; (▽) IV-2; and (▼) IX-2. In FIG. 4A thioredoxin 0.7 μM was incubated with 3.4 μM disulfide in 100 mM HEPES buffer, pH 7.4, 5 mM EDTA at room temperature for up to 24 hr before adding thioredoxin reductase at 2.8 μg/ml, insulin 1 mg/ml and NADPH 140 mM. FIG. 4B shows preincubation of 3.5 mM disulfide with thioredoxin reductase, 2.8 μg/ml under the same buffer conditions for up to 24 hr before the addition of thioredoxin 0.7 mM, insulin 1 mg/ml and NADPH 140 mM. All trials were done in triplicate.

As can be seen in FIGS. 4A and 4B, preincubation of the disulfides with thioredoxin resulted in a loss of the ability of thioredoxin to be reduced by thioredoxin reductase with half lives for the loss by III-2 being 30 min, IV-2 being 4 hr and IX-2 being 24 hr.

Figure 5:
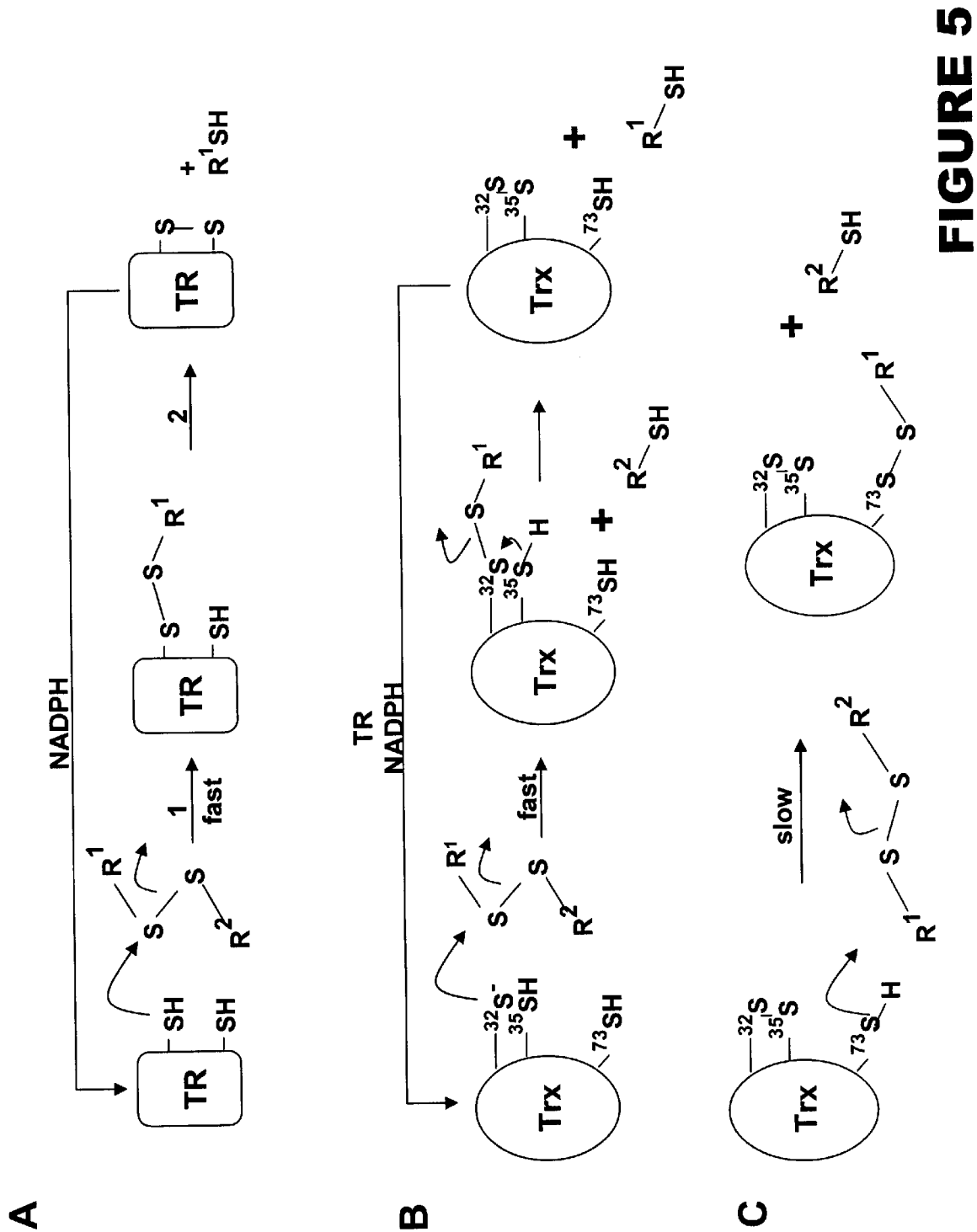
FIG. 5 illustrates proposed scheme for the reaction of the disulfides ($R_1SSR_2$) with thioredoxin reductase and thioredoxin.

Dialyzing the thioredoxin against buffer for 24 hr after reaction with the disulfides failed to reverse the inhibition. C73S showed no loss of the ability to be a substrate for thioredoxin reductase by exposure to any of the disulfides for 24 hr. Electrophoretic analyses of thioredoxin following 24 hr exposure to III-2 and IV-2 showed no evidence of increased homodimer formation over that produced during the 2 hr exposure. The results suggests that the disulfides cause irreversible thiolation of thioredoxin, probably at $Cys^{73}$, resulting in a loss of the ability of thioredoxin to be reduced by thioredoxin reductase. Evidence that the effect is specific for thioredoxin and not a general inactivation of proteins by the disulfides, is the absence of inhibition by preincubation of the disulfides with thioredoxin reductase as seen in FIG. 5 or glutathione reductase.

The asymmetric disulfides of the present invention appear to interact with both thioredoxin reductase and thioredoxin. While not intending to be bound by theory, it is postulated that the unbranched alkyl moieties of the disulfides III-2 and VI-2, both of which are substrates for thioredoxin reductase, facilitates thiol/disulfide exchange with a Cys residue at the catalyic site of thioredoxin reductase and the liberation of 2mercaptoimidazole (FIG. 5A). There is a subsequent thiol/disulfide exchange to give an oxidized catalytic site followed by reduction by NADPH to regenerate the reduced enzyme. Branching of the alkyl substituent of IV-2 and the benzyl group of DLK 36, prevents these compounds from readily undergoing the second thio/disulfide exchange so that these agents are weak competitive inhibitors of the TR/Trx system. Extensive branching, as with the t-butyl analog, IX-2, decreased the reactivity of the disulfide towards the catalytic site Cys residues of thioredoxin reductase and prevents IX-2 from acting as either a substrate or inhibitor.

There is a rapid reaction of the disulfides with Trx and liberation of 2-mercaptoimidazole, most likely at the conserved active site $Cys^{32}$ of thioredoxin which has been shown to have a lower pKa than $Cys^{35}$ and is thought to exist as the thiolate anion. Evidence that the catalytic site is the site of this reaction is that the C32S/C35S mutant thioredoxin does not undergo this reaction. As can be seen in FIG. 5B, the thioalkylated derivative or the oxidized thioredoxin following a second thiol-disulfide exchange, remains a substrate for reduction by thioredoxin reductase. A slower and irreversible reaction between the disulfides and thioredoxin results in thioredoxin's inactivation as a substrate for thioredoxin reductase (see FIG. 5C) and ultimately the inhibition of the thioredoxin reductase/thioredoxin system. The inhibition is not seen when C73S is substituted for thioredoxin in the reaction suggesting that the reaction occurs at $Cys^{73}$. C73S is as effective as thioredoxin as a substrate for reduction by thioredoxin reductase. Further evidence that thiolation occurs at $Cys^{73}$ is that the disulfides block homodimerization of thioredoxin caused by diamide, involves $Cys^{73}$ homodisulfide bond formation. Thus, the results suggest that while the hydroxyl group of $Ser^{73}$ allows reduction of the conserved redox active site of C73S by thioredoxin reductase, thioalkylation of the $Cys^{73}$ in thioredoxin inhibits this activity. The basis for this inhibition is not clear but presumably, involves a steric block of the interaction of $Cys^{73}$ with thioredoxin reductase. Thioredoxin reductase has recently been shown to have an unusual selenocysteine group at its C-terminal end which appears to be essential for catalytic activity. Possibly, an interaction occurs between this selenocysteine and $Cys^{73}$ of thioredoxin.

The selectivity of some of the asymmetric disulfides of the present invention, specifically the 2-imidazolyl disulfides appear to be supported by the fact that they are irreversible inhibitors of thioredoxin but not of thioredoxin reductase or glutathione reductase. This is presumably because thiolation of the catalytic site cysteine of these enzymes is a reversible process, while the thiolated Cys73 residue of thioredoxin is outside the catalytic site. The thioredoxin system is widely distributed in tissue and it is likely the assymetric disulfides will be selective in their effect on cancer cell over expressing thioredoxin compared to normal cells. The disulfides have shown in vivo antitumor activity against human tumor xenografts in scid mice. These assymetric agents may show tissue and cancer types specificity in those cancers which overexpress thioredoxin compared to those which are hyperproliferating for other reasons.

As it is illustrated above, the disulfides of the present invention inhibit the growth of a number of cancer cell lines in culture. In addition, the growth of a number of human primary tumors in soft agarose was inhibited by IV-2, which showed selectivity for myeloma, cervical and breast cancer.

Figure 6:
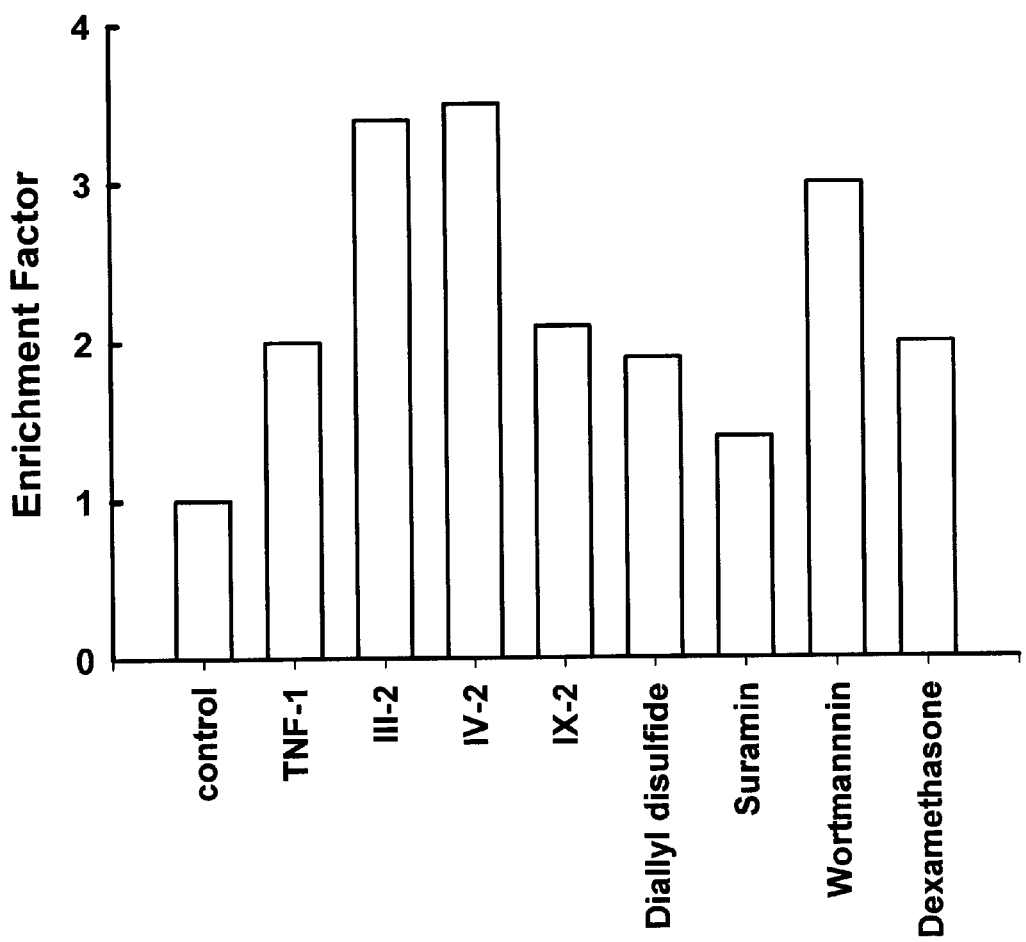
FIG. 6 illustrates induction of apoptosis in HT-29 colon cancer cells over 48 hours.
Figure 7:
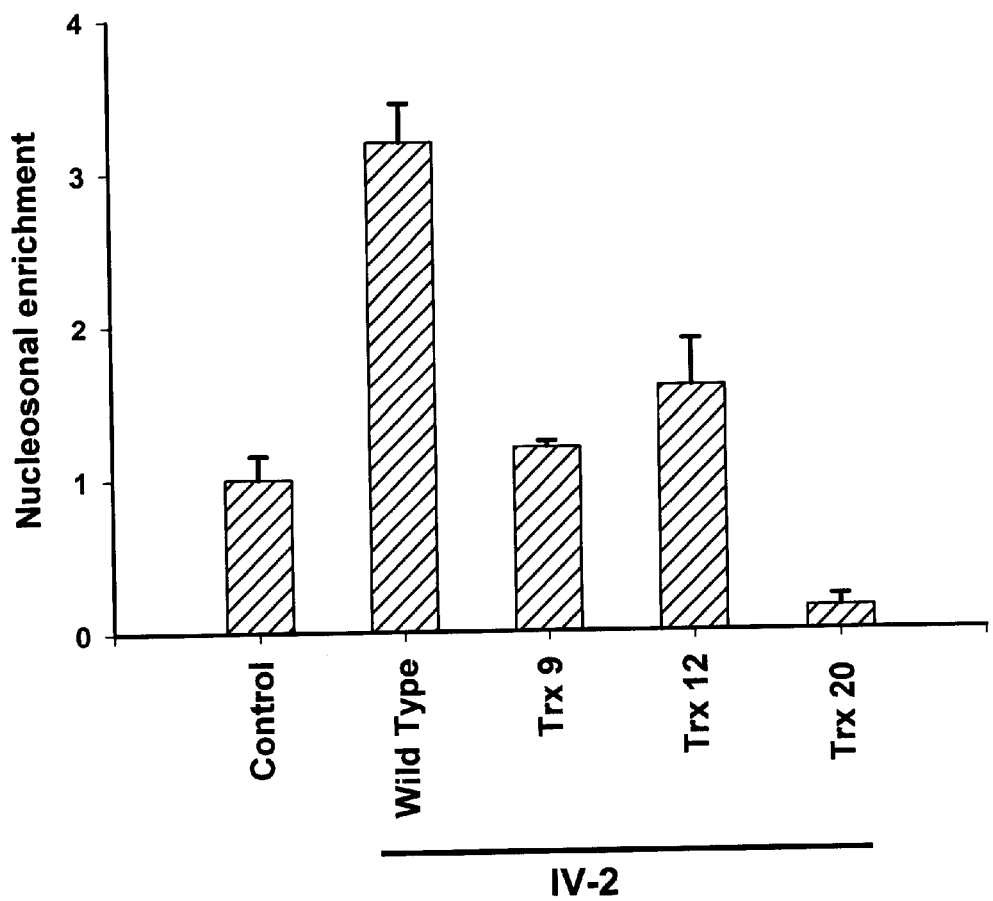
FIG. 7 illustrates IV-2 (F-1) induced apoptosis by thioredoxin transfection.
Figure 8:
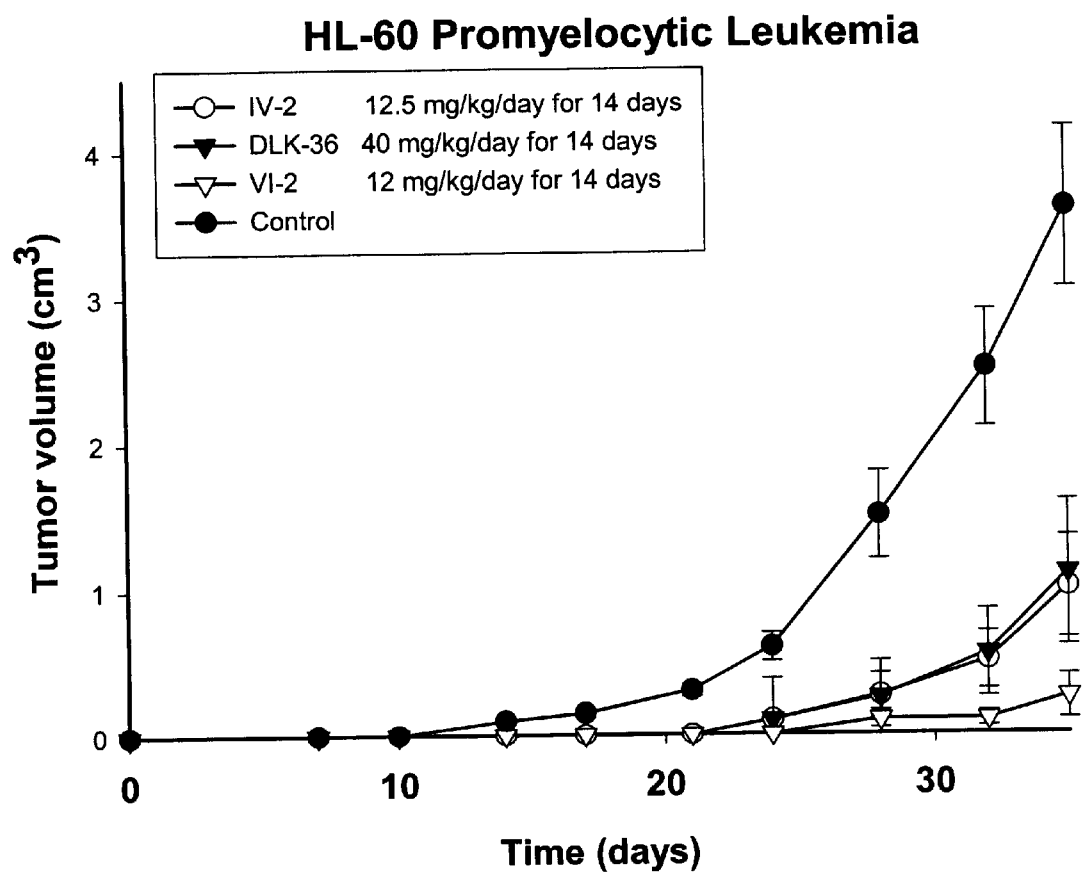
FIG. 8 illustrates anti-tumor activity of disulfides against HL-60 promyelocytic leukemia growing in scid mice with (●)vehicle alones, (○) IV-2 12.5 mg/kg/day, (▼) DLK-36 40 mg/kg/day, (▽) VI-2 12 mg/day.

HL60 cells treated with the butyl analogs, III-2 or IV-2, are stimulated to apoptose within 8 h of exposure, whereas the t-butyl 2-imidazolyl disulfide, IX-2 does not cause apoptosis at the same concentration in the same time frame. A correlation with the thioalkylating ability of these disulfides shows that IX-2 is three logs slower than III-2 to undergo thiol/disulfide exchange reaction with thioredoxin. Pretreatment of the HL60 cells with the antioxidant, N-acetylcysteine for 13 h prior to exposure to III-2, prevented apoptosis. Apoptosis is thought to mediate normal cell turnover, hormone-induced tissue atrophy, cell mediated killing immunity and tumor regression. As shown in FIG. 6, the 2-imidazolyl disulfides are among the most potent inducers of apoptosis found from among a series of known apoptosis-inducing agents we tested. Moreover, as can be seen in FIG. 7, the thioredoxin transfected MCF-7 cells became resistant to apoptosis induced by IV-2. Thus, the effects of disulfides in inducing apoptosis appear to involve a redox mechanism and thioredoxin.

The lead compound, IV-2, and some analogues have been shown to exhibit dose-dependent antitumor activity against human MCF-7 breast cancer and HL-60 xenografts growing in scid mice. This is shown below in Table II.

TABLE 2

Activity against MCF-7 breast cancer cells in scid mice.

| Compound | Dosage mg/kg/day for 14 days | T/C[b] % | Toxicity dead/injected |
|---|---|---|---|
| III-2 | 6 | 48.9[c] | 0/8 |
|  | 12 | 56.6[c] | 0/8 |
|  | 18 | 100.2 | 1/8 |
| IV-2 | 5 | 56.7 | 2/8 |
|  | 10 | 45.9[c] | 0/7 |
|  | 15 | 2.3[c] | 0/7 |
| VI-2 | 4 | 83.0 | 1/8 |
|  | 6 | 65.8 | 0/8 |
|  | 12 | 64.6 | 4/8 |
| DLK-36 | 25 | 100.7 | 1/8 |
|  | 40 | 23.7[c] | 0/6 |

[a] i.p. daily for 14 days starting day 1
[b] tumor volume of treated versus control at day 28
[c] p < 0.005

The disulfides IV-2 and DLK-36 produced responses of 98% and 65% tumor inhibition respectively against the MCF-7 tumor system. In FIG. 7 MCF-7 human breast cancer cells transfected with human thioredoxin cDNA were treated with 30 μM IV-2 and apoptosis was measured 48 h later. Wild type refers to cells transfected with vector alone. Three of the disulfides, IV-2, VI-2 and DLK-36 all showed antitumor activity against HL-60 leukemia growing in scid mice with a number of the animals without tumor cells were inoculated s.c. on day 0 and drug administration was commenced on day 1 for 14 days at day 45 for each compound. These results are shown in FIG. 7. MCF-7 human breast cancer cells transfected with human thioredoxin cDNA were treated with 30 μM IV-2 and apoptosis was measured 48 h later. Wild type refers to cells transfected with vector alone.

Based on the information provided by studying the asymmetrical imidazoyl disulfides (i.e., VI-2) a parallel combinatorial synthetic method was used to produce a large number of disulfide analogues to study specificity and applicability to the thioredoxin. These analogues, which differ sterically, electronically and physically, were produced in a 96 well plate. The biological activity of these analogues was evaluated, also in the 96 well plate format. This rapid method of evaluating biological activity is a means to identify agents with specificity for inhibition of the thioredoxin system, and as evidenced herein provide novel antitumor agents with activity against solid tumor cancers.

The asymmetrical disulfides are of the general formula of $R_1$—S—S—$R_2$ wherein $R_1$ and $R_2$ are not the same independently represent an alkyl, an arylalkyl, an imidazole thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone. The asymmetrical disulfides may also be (bis)disulfide type, generally represented by the formula $R_1$—S—S—Y—S—S—$R_2$, wherein $R_1$ and $R_2$ and Y may be the same and are independently selected from the group described above with Y preferably being selected from the group consisting of alkyl, hydroxyalkyl, arylalkyl, and thiadiazoles. $R_1$, and $R_2$ may be for example any of the substituents shown in FIG. 9 and FIG. 10.

Asymmetric disulfides of this type have been synthesized. The general formulas of the preferred asymmetric disulfides of the present invention, along with preferred disulfides of the respective groups along with their codes are shown below in Table 3.

TABLE 3

| General Formula | Representative Disulfide | Code | IC$_{50}$ TR/Trx μg/ml | μM |
|---|---|---|---|---|
|  |  |  |  | Toxicity |
| 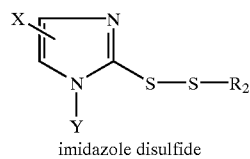 imidazole disulfide | 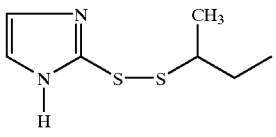 | F-1 | 7 | 19 |
| 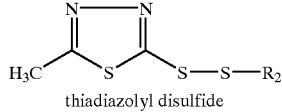 thiadiazolyl disulfide | 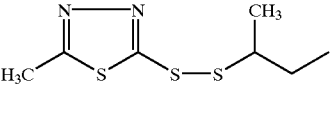 | F-3 | 15 | 7 |
| 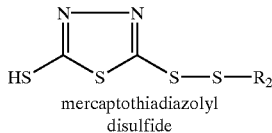 mercaptothiadiazolyl disulfide | 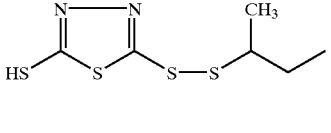 | F-4 | 28 | 36 |

TABLE 3-continued
| General Formula | Representative Disulfide | Code | IC$_{50}$ TR/Trx μg/ml | μM |
|---|---|---|---|---|
|  thiazolyl disulfide |  | F-5 | ND | 34 |
| 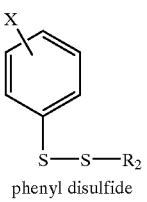 phenyl disulfide | 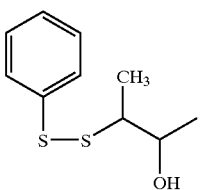 | M-13 | ND | 46 |
| 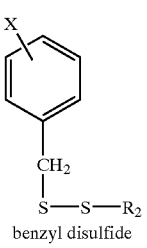 benzyl disulfide | 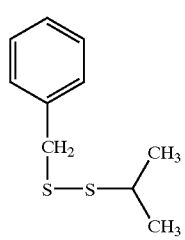 | E-19 | ND | 42 |
| 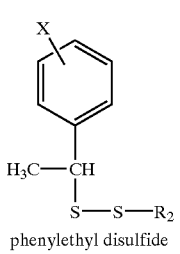 phenylethyl disulfide | 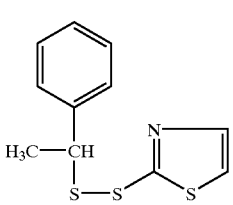 | J-1 | 4 | 28 |
| | | | | Cytotoxicity |
|---|---|---|---|---|
| 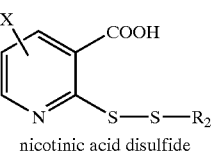 nicotinic acid disulfide | 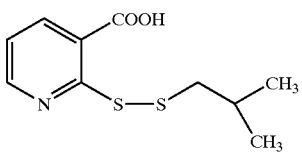 | G-23 | 14 | ND |
| 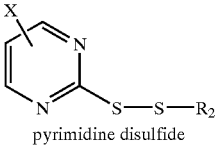 pyrimidine disulfide | 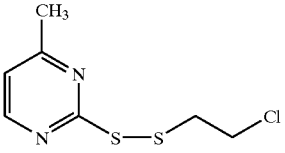 | H-24 | ND | 73 |
| 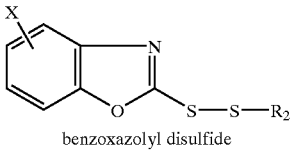 benzoxazolyl disulfide | 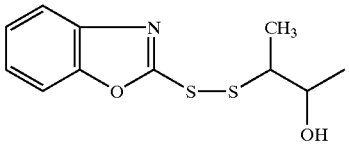 | M-29 | ND | 29 |
| 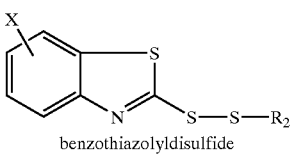 benzothiazolyldisulfide | 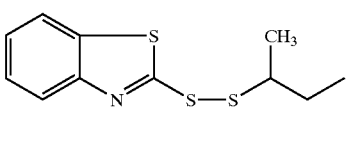 | F-11 | ND | 33 |

TABLE 3-continued

| General Formula | Representative Disulfide | Code | IC$_{50}$ TR/Trx μg/ml | μM |
|---|---|---|---|---|
| 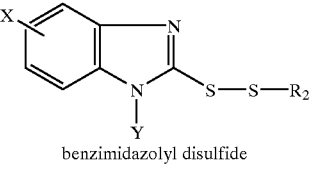 benzimidazolyl disulfide | 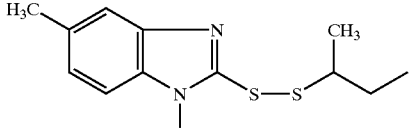 | F-9 | 9 | 55 |
| 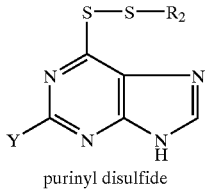 purinyl disulfide | 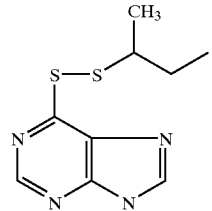 | F-7 | 23 | >180 |
| 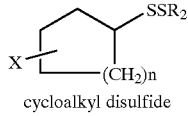 cycloalkyl disulfide | 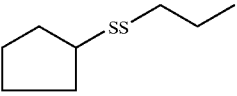 | F-27 | ND | 51 |
| 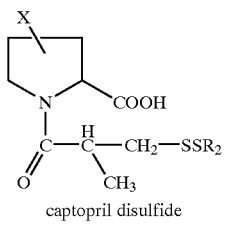 captopril disulfide | 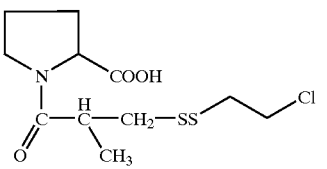 | H-28 | ND | 62 |
| 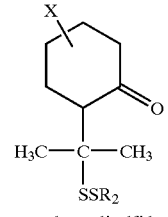 menthone disulfide | 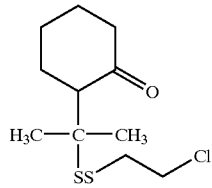 | H-26 | ND | 68 |

Generally, the X group may be any common functional group, but preferably is selected from the group consisting of alkyl, alkoxy, hydroxy, carboxy, carbaldehyde, amino, halo, keto, nitro and combinations thereof. Thus, it is preferred that a disulfide selected from the group consisting of imidazole disulfide, thiadiazolyl disulfide, mercaptothiadiazolyl disulfide, thiazolyl disulfide, phenyl disulfide, benzyl disulfide, phenylethyl disulfide, nicotinic acid disulfide, pyrimidine disulfide, benzoxazolyl disulfide, benzothiazolyl disulfide, benzimidazolyl disulfide, purinyl disulfide, cycloalkyl idsulfide, captopril disulfide, and menthone disulfide. As mentioned above, the term asymmetric disulfide includes salts thereof such as hydrohalide, acetate, sulfonate, tosylate, phosphate, etc.

Figure 9:
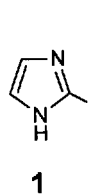
FIG. 9 illustrates R groups which may be substituents $R_1$ and $R_2$ in the disulfide and (bis)disulfide formulas of the present invention.
Figure 9:
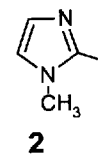
Figure 9:
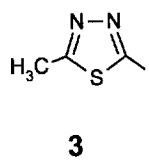
Figure 9:
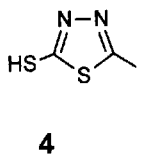
Figure 9:
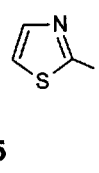
Figure 9:
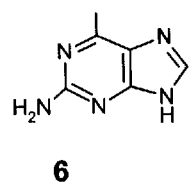
Figure 9:
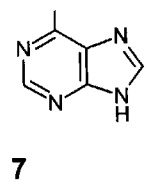
Figure 9:
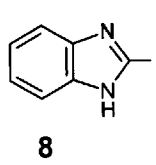
Figure 9:
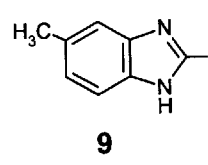
Figure 9:
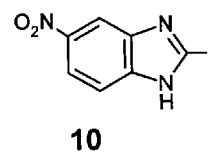
Figure 9:
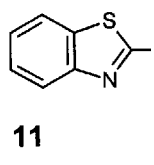
Figure 9:
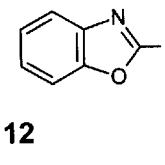
Figure 9:
Figure 9:
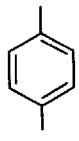
Figure 9:
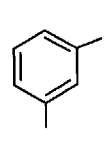
Figure 9:
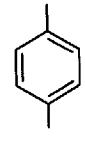
Figure 9:
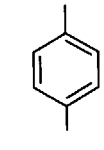
Figure 9:
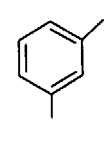
Figure 9:
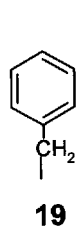
Figure 9:
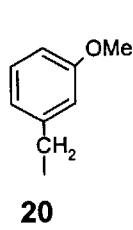
Figure 9:
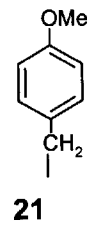
Figure 9:
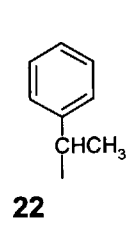
Figure 9:
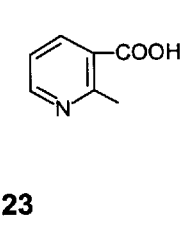
Figure 9:
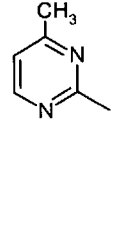
Figure 9:
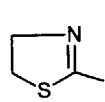
Figure 9:
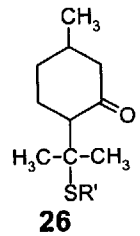
Figure 9:
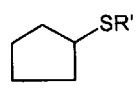
Figure 9:
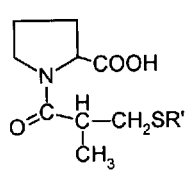
Figure 10:
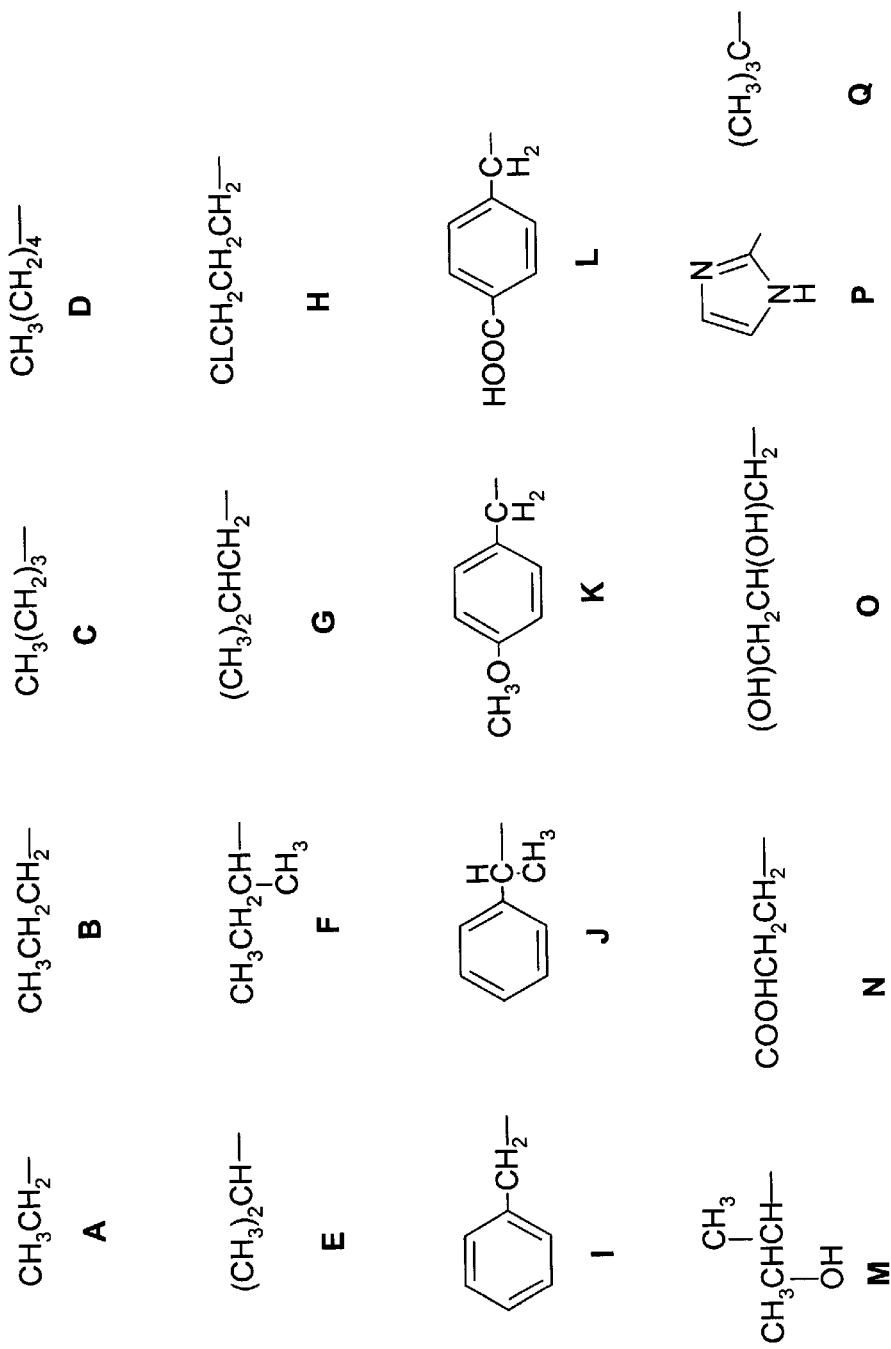
FIG. 10 illustrates $R^1$ groups which may be substituents $R_1$ and $R_2$ in the disulfide and (bis)disulfide formulas of the present invention.

The code used in Table 3 is to be read in conjunction with FIGS. 9 and 10. This is the case throughout the specification. For example, a compound referred to as A-7 has one of $R_1$ or $R_2$ an ethyl substituent and as the other a purine substituent.

Using a 96 well plate format, parallel combinatorial chemistry similar to that described by Borman S., Chem. Eng. News, 74:29–64 (1996) which is incorporated herein by reference in its entirety was used to synthesize a large number of unsymmetrical disulfides. The activated alkyl thiols were synthesized as previously described in Kirkpatrick et al. Eur. J. Med. Chem. 27:33–37 (1992) also hereby incorporated by reference in its entirety. In a 96 well format, these alkylthioisothiourea HCl salts were dissolved in methanol and 5.2 mmol of each placed in rows on 96 well plates. To each well was added 4 additions of 35 ml of 50 mM NaHCO$_3$ (final volume 200 ml) with 45 min stirring in between additions and 2 hr following the final addition. The plates were placed in a freezer (−20° C.) overnight, then centrifuged at 1500×g for 30 min and the solvent carefully removed. The resultant precipitate was dried under a stream of N$_2$ gas and plates were placed in a vacuumed desiccator. Using one of the plates, analytical procedures (TLC and NMR) were carried out on the product of each well and indicated that the desired products were obtained.

A second plate was used for the assessment of biological activity or as a biological screen. Aliquots of disulfides dissolved in DMSO, were be transferred into 96 well plates. The assay to assess their ability to inhibit thioredoxin reductase measures the thioredoxin dependent reduction of insulin by human thioredoxin reductase and NADPH. The effects of the disulfides on the reduction of Trx by TR were measured spectrophotometrically by following the reduction of NADPH at 339 nm with insulin as the final electron acceptor in a buffered mixture of TR, Trx, NADPH and insulin.

Table 4 below shows the $IC_{50}$ TR/Trx of select asymmetric disulfides. The $IC_{50}$ data is expressed in terms of $\mu g/ml$

TABLE 4

Disulfide inhibition of TR/Trx ($\mu g/ml$)

| | A | B | C | E | F | G | I | J |
|---|---|---|---|---|---|---|---|---|
| 1 | 4 | 7 | 22 | 7 | 7 | 8 | 40 | 4 |
| 2 | 80 | 75 | 147 | 100 | 51 | 125 | 100 | 12 |
| 3 | 75 | 85 | 9 | 100 | 15 | 29 | 9 | 11 |
| 4 | 35 | 35 | 56 | 35 | 28 | — | 5 | 42 |
| 5 | — | — | — | — | — | — | — | — |
| 6 | — | — | 33 | — | — | — | — | 38 |
| 7 | — | — | 33 | — | 23 | — | — | — |
| 8 | — | — | 57 | — | 7 | 18 | — | 8 |
| 9 | — | — | 12 | — | 9 | 11 | — | 43 |
| 10 | — | — | >76 | — | 47 | — | — | 43 |
| 11 | — | — | — | — | — | — | — | — |
| 12 | — | — | 42 | — | 22 | 52 | — | 16 |
| 13 | — | — | — | — | — | — | — | — |
| 14 | — | — | — | — | — | — | — | — |
| 15 | — | — | — | — | — | — | — | — |
| 16 | — | — | — | — | — | — | — | — |
| 17 | — | — | 179 | — | 203 | 203 | — | 246 |
| 18 | — | — | — | — | — | — | — | — |
| 19 | — | — | >189 | — | >189 | >189 | — | >232 |
| 20 | — | — | 61 | — | 61 | — | — | 74 |
| 21 | — | — | 179 | — | 60 | >203 | — | 74 |
| 22 | — | — | 194 | — | 201 | 201 | — | — |
| 23 | 35 | — | 65 | 40 | 81 | 14 | 35 | 89 |
| 24 | 90 | — | 48 | 60 | 83 | 65 | 35 | 67 |
| 25 | — | — | — | — | — | — | — | — |
| 26 | — | — | — | — | — | — | — | — |
| 27 | — | — | 51 | — | 51 | — | — | 64 |
| 28 | — | — | — | — | — | — | — | — |

Table 5 illustrates the $IC_{50}$ cytotoxicity of select asymmetric disulfides against EMT6 mouse mammary tumor cells grown in cultures. The cytoxicity is expressed in $\mu M$ and the Letter-number format corresponds to FIG. 9 and FIG. 10.

TABLE 5

Disulfide Cytotoxicity $\mu M$

| | A | B | C | E | F | G | H | I | J | M | N |
|---|---|---|---|---|---|---|---|---|---|---|---|
| 1 | 8 | 21 | 12 | 24 | 19 | 28 | >180 | 22 | 28 | 34 | 100 |
| 2 | 15 | — | 26 | 33 | 43 | — | >180 | — | — | 180 | 180 |
| 3 | — | — | — | >180 | 7 | — | >180 | — | — | 180 | 91 |
| 4 | — | — | — | — | 36 | — | — | — | — | — | — |
| 5 | — | — | — | — | 34 | — | — | — | — | — | — |
| 6 | — | — | — | 42 | 23 | — | 25 | — | — | 32 | 20 |
| 7 | — | — | — | >180 | >180 | — | 36 | — | — | 180 | 180 |
| 8 | — | — | — | 66 | 73 | — | 82 | — | — | 180 | 180 |
| 9 | — | — | — | >180 | 55 | — | 66 | — | — | 76 | 85 |
| 10 | — | — | — | 29 | 36 | — | 59 | — | — | 34 | 103 |
| 11 | — | — | — | — | 33 | — | — | — | — | — | — |
| 12 | — | — | — | >180 | >180 | — | >180 | — | — | 29 | 180 |
| 13 | — | — | — | >180 | >180 | — | >180 | — | — | 46 | 83 |
| 14 | — | — | — | — | — | — | — | — | — | — | — |

TABLE 5-continued

Disulfide Cytotoxicity $\mu M$

| | A | B | C | E | F | G | H | I | J | M | N |
|---|---|---|---|---|---|---|---|---|---|---|---|
| 15 | — | — | — | 102 | >180 | — | 106 | — | — | 180 | 180 |
| 16 | — | — | — | 66 | — | — | 78 | — | — | 43 | 74 |
| 17 | — | — | — | 102 | — | — | 106 | — | — | 82 | 108 |
| 18 | — | — | — | 42 | — | — | 47 | — | — | 180 | 180 |
| 19 | — | — | — | 25 | 108 | — | 108 | — | — | 91 | 68 |
| 20 | — | — | — | >180 | >180 | — | 91 | — | — | — | — |
| 21 | — | — | — | — | — | — | — | — | — | — | — |
| 22 | — | — | — | >180 | >180 | — | 73 | — | — | 180 | 90 |
| 23 | — | — | — | >180 | >180 | — | 69 | — | — | 96 | 92 |
| 24 | — | — | — | >180 | >180 | — | 73 | — | — | 180 | 180 |
| 25 | — | — | — | — | 31 | 38 | — | — | — | — | — |
| 26 | — | — | — | >180 | >180 | — | 68 | — | — | 180 | 180 |
| 27 | — | — | — | — | — | — | — | — | — | — | — |
| 28 | — | — | — | >180 | >180 | — | 62 | — | — | 180 | 180 |

To determine cytotoxicity against EMT6 mouse mammary tumor cells grown in culture, the following methodology was used.

EMT6 mouse mammary carcinoma cells were maintained in Waymouth's medium containing 15% Clex (semisynthetic serum; Dextran Products) and passage twice as week. Cells were trypsinized, counted and 1500 cells were placed in each well of 96-well plates in a final volume of 180 ul and allowed to grow for 48 h (37° C.; 5% $CO_2$). Each disulfide in the drug synthesis 96-well plates was dissolved in dimethylsulfoxide (DMSO) to give final concentration of 10 mM. Disulfides were diluted in sterile phosphate buffered saline (PBS; pH 7.2). Drug (20 ul) or vehicle (40 ul DMSO in 160 ul PBS) was transferred into wells with activly growing EMT6 cells. Control wells of cells alone or medial blanks were also used. Plates were incubated for another 48 h (37oC; 5% $C0_2$), following which 20 ul of MTT (5 mg/ml) was added to each well. The plates were incubated another 4 h, then centrifuged at 2000 rpm for 10 min. The supernatant was removed from all wells, the plate inverted and lotted dry to remover residual medium. DMSO (200 ul) was added to each well and the plates were shaken for 10 min to dissolve formazan crystals.

OD readings were taken using a EAR 96- well plate reader at 455 nm, ref 650 nm. The $IC_{50}$ was determined as that concentration of disulfide which decreased growth of EMT6 cells by 50% of that of control.

Figure 11:
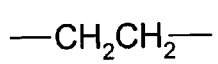
FIG. 11 illustrates groups which may preferably be substituents Y in the bis disulfide general formulas of the present invention.
Figure 11:
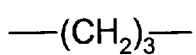
Figure 11:
Figure 11:
Figure 11:
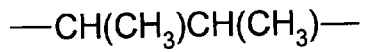
Figure 11:
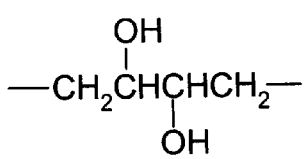
Figure 11:
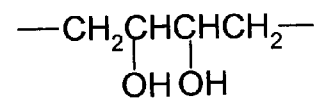
Figure 11:
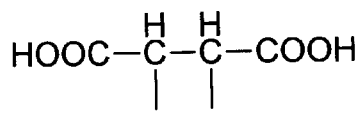
Figure 11:
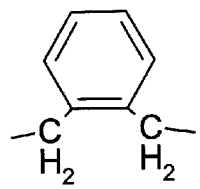
Figure 11:
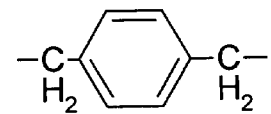
Figure 11:
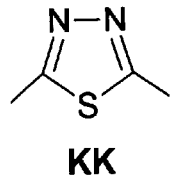

IC50 TR/Trx data and cytotoxicity data for select (bis) disulfide compounds of the present invention are shown below in Table 6. Italicized and bold (i.e., CC-1 and DD-3) illustrate $IC_{50}$ TR/Trx in $\mu g/ml$ and regular type (i.e., AA-1) show cytotoxicity data in $\mu M$. For convenience, the toxicity data is shown in bold. In Table 6, the number code refers to the R groups in FIG. 9 and the letter codes (i.e., AA) refer to the compounds in FIG. 11. In the general formula $R_1$—S—S—Y—S—S—$R_2$, $R_1$ and $R_2$ are preferably selected from FIG. 9 and Y is preferably selected from FIG. 11.

TABLE 6

(Bis) Disulfide Compounds

| | AA | BB | CC | DD | EE | FF | GG | KK |
|---|---|---|---|---|---|---|---|---|
| 1 | 55 | >180 | 37 | 3 | 16 | >180 | >180 | — |
| 2 | 102 | >180 | 147 | 7 | 20 | >180 | >180 | — |
| 3 | >180 | >180 | 9 | 5 | 12 | >180 | >180 | — |

TABLE 6-continued

(Bis) Disulfide Compounds

| | AA | BB | CC | DD | EE | FF | GG | KK |
|---|---|---|---|---|---|---|---|---|
| 4 | — | — | — | — | — | — | — | — |
| 5 | — | — | — | — | — | — | — | — |
| 6 | 27 | 36 | — | — | — | 76 | 27 | — |
| 7 | 54 | >180 | 36 | 7 | 9 | >180 | >180 | — |
| 8 | 52 | >180 | 217 | 16 | 89 | >180 | >180 | — |
| 9 | 56 | >180 | — | — | — | >180 | >180 | — |
| 10 | 76 | — | 68 | 14 | 51 | — | 18 | — |
| 11 | — | — | — | — | — | — | — | — |
| 12 | 108 | >180 | 109 | 5 | 67 | >180 | >180 | — |
| 13 | 35 | 76 | — | — | — | >180 | 90 | — |
| 14 | — | — | — | — | — | — | — | — |
| 15 | 26 | 89 | — | — | — | 95 | 96 | — |
| 16 | 25 | 50 | — | — | — | 62 | 50 | — |
| 17 | 54 | 86 | 53 | 55 | 53 | 82 | 86 | — |
| 18 | 31 | >180 | — | — | >180 | 82 | — | — |
| 19 | 52 | 115 | >326 | 193 | 222 | 35 | 35 | — |
| 20 | — | — | — | — | — | — | — | — |
| 21 | — | — | 174 | 274 | 220 | — | — | — |
| 22 | 72 | >180 | >355 | 256 | 195 | 17 | 18 | 42 |
| 23 | >180 | >180 | 129 | 85 | 89 | >180 | >180 | — |
| 24 | 34 | 39 | 32 | 4 | 27 | >180 | >180 | — |
| 25 | — | — | — | — | — | — | — | — |
| 26 | >180 | >180 | — | — | — | >180 | >180 | — |
| 27 | — | — | 43 | 45 | 43 | — | — | — |
| 28 | 65 | >180 | — | — | — | >180 | >180 | — |
| C | — | — | — | — | — | — | — | >87 |
| F | — | — | — | — | — | — | — | 28 |

The unsymmetrical disulfides of the present invention have been shown to inhibit thioredoxin stimulated growth in vitro and display anti-tumor activity in vivo. It has been proposed that the inhibition is the result of thioalkylation of the active site cysteine residues. Disulfide moieties are critical for this inhibition through a thiol/disulfides exchange reaction and the aromatic and alkyl portions of the molecules confer potency and specificity by affecting the rates of reactivity.

The method of the present invention involves administering to a mammalian host, preferably a human host, pharmacologically effective amounts of asymmetric disulfide. The asymmetric disulfides may be combined in vitro before administration or separately administered to the host with other anti-cancer agents, either concurrently or simultaneously, with administration generally taking place up to 24 hours before or after the administration of the other biological active agent(s).

The administration(s) may take place by any suitable technique, including oral, subcutaneous and parenteral administration, preferably parenteral or oral. Examples of parenteral administration include intravenous, intra-arterial, intramuscular, and intraperitoneal, with intraperitoneal and intravenous being preferred. The dose and dosage regimen will depend mainly on whether the inhibitors are being administered for therapeutic or prophylactic purposes, separately or as a mixture, the type of biological damage and host, the history of the host, and the type of inhibitors or biologically active agent. The amount must be effective to achieve an enhanced therapeutic index as defined above. It is noted that humans are treated longer than the mice and rats with a length proportional to the length of the disease process and drug effectiveness. The doses may be single doses or multiple doses over a period of several days, but single doses are preferred. Therapeutic purposes is achieved as defined herein is when the treated hosts exhibit improvement against disease or infection, including but not limited to improved survival rate, more rapid recovery, or improvement or elimination of symptoms. If multiple doses are employed, as preferred, the frequency of administration will depend, for example, on the type of host and type of cancer, dosage amounts, etc. For some types of cancers or cancer lines, daily administration may be effective, whereas for others, administration every other day or every third day may be effective, but daily administration ineffective. The practitioner will be able to ascertain upon routine experimentation which route of administration and frequency of administration are most effective in any particular case. The dosage amounts for cancer which appear to be most effective herein are those that result in regression in size of the tumor or complete disappearance or non-reappearance of the tumor, and are not toxic or are acceptably toxic to the host patient. The optimum dose levels may also depend on sequence of administration, existing tumor burden, are the type of precursor.

Compounds and agents of the present invention, in conjunction with a pharmaceutically acceptable carrier, may be used for any of the therapeutic effects, discussed above. Such compositions may be in the form of an agent in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. Pharmaceutically-acceptable carriers may also be comprised of excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.) hereby incorporated herein by reference in its entirety.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing-agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvents mixtures. Dyestuffs or pigments may be added to the tablets or dragee coatings for product identification or to characterize the quantity of active compound. i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition, For administration of thioredoxin reductase/Trx inhibitors, such labeling would include amount, frequency, and method of administration.

For any of the asymmetric disulfide compounds discussed herein, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

The exact dosage will be determined by the practitioner, in light of factors related to the subject that requires treatment. Dosage and administration are adjusted to provide sufficient levels of the active moiety. or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 up to about 100,000 micrograms depending upon the route of administration. Guidance as to particular dosages and methods of delivery is provided in the literature and herein as well as generally available to practitioners in the art.

It is anticipated that as the understanding of the asymmetric disulfides of the present invention as well as cellular redox systems and their role in the control of cell growth advances, new targets for anti-cancer drug development will emerge. The link between external stimuli and activation of growth, cell death and transformation, through redox modulation is growing. The possibility of reversing the uncontrolled growth of tumors through control of redox signaling, or committing a cell to die by the redox regulation of factors involved in cell death provide intriguing prospects for drug development.

While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein. For example, it is specifically contemplated herein that the asymmetric disulfides may be modified to fluoresce and used as a tag to monitor the thioredoxin/thioredoxin reductase system. Additionally, it is specifically contemplated herein that the disulfides of the present invention may be incorporated into a mesh column to separate or isolate proteins or enzymes of a redox system, particularly a thioredoxin redox system.

What is claimed is:

1. A compound represented by the formula:

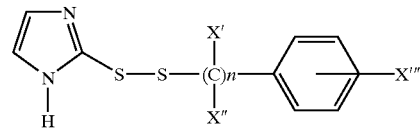

wherein n is 1 or 2 and X', X", X''' each is selected from the group consisting of hydrogen, alkyl, aryl, alkoxy, hydroxy, carboxy, carbaldehyde, amino, halo, keto, and nitro.

2. The compound of claim 1, wherein n is equal to 1 and X' and X" are each hydrogen, said compound having the formula:

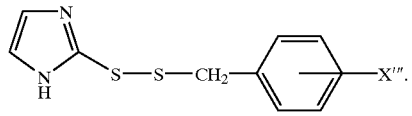

3. The compound of claim 2, represented by the formula:

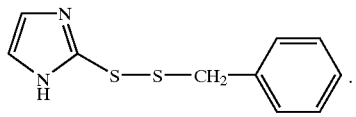

4. The compound of claim 2, represented by the formula:

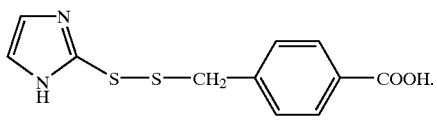

5. The compound of claim 1, wherein said compound has an $IC_{50}$ Tr/Trx value of less than about 150 µg/ml.

6. The compound of claim 1, as a salt.

7. The compound of claim 6, wherein said salt is selected from the group consisting of hydrohalide, acetate, sulfonate, tosylate, and phosphate.

8. A compound of a general formula:

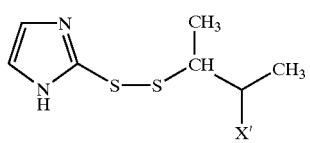

wherein X' is selected from the group consisting of hydroxy, alkyl, alkoxy, carboxy, carbaldehyde, amino, halo, keto, and nitro.

9. The compound of claim 8, wherein said compound has an $IC_{50}$ Tr/Trx value of less than about 150 µg/ml.

10. The compound of claim 8, as a salt.

11. The compound of claim 10, wherein said salt is selected from the group consisting of hydrohalide, acetate, sulfonate, tosylate, and phosphate.

12. A compound having a general formula:

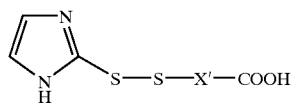

wherein X' is selected from the group consisting of an alkyl, aryl, phenyl, or substituted form thereof.

13. The compound of claim 12, having the formula:

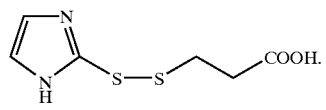

14. The compound of claim 12, having the formula:

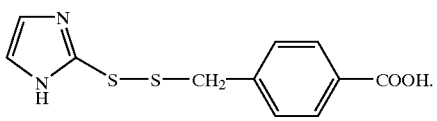

15. The compound of claim 12, wherein said compound has an $IC_{50}$ Tr/Trx value of less than about 150 µg/ml.

16. The compound of claim 12, as a salt.

17. The compound of claim 16, wherein said salt is selected from the group consisting of hydrohalide, acetate, sulfonate, tosylate, and phosphate.

18. A compound represented by the formula:

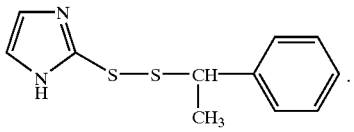

19. A compound represented by the formula:

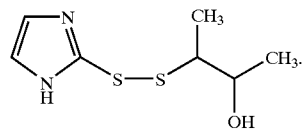

* * * * *